US012411124B2

(12) United States Patent
Lei et al.

(10) Patent No.: US 12,411,124 B2
(45) Date of Patent: Sep. 9, 2025

(54) SYSTEM FOR SEQUENCING BIOPOLYMERS

(71) Applicant: Universal Sequencing Technology Corporation, Canton, MA (US)

(72) Inventors: Ming Lei, Sharon, MA (US); Peiming Zhang, Gilbert, AZ (US)

(73) Assignee: UNIVERSAL SEQUENCING TECHNOLOGY CORPORATION, Canton, MA (US)

( * ) Notice: Subject to any disclaimer, the term of this patent is extended or adjusted under 35 U.S.C. 154(b) by 928 days.

(21) Appl. No.: 17/424,969

(22) PCT Filed: Nov. 27, 2019

(86) PCT No.: PCT/US2019/063803
§ 371 (c)(1),
(2) Date: Jul. 22, 2021

(87) PCT Pub. No.: WO2020/113138
PCT Pub. Date: Jun. 4, 2020

(65) Prior Publication Data
US 2022/0091094 A1    Mar. 24, 2022

Related U.S. Application Data

(60) Provisional application No. 62/772,837, filed on Nov. 29, 2018.

(51) Int. Cl.
| G01N 33/487 | (2006.01) |
| B82Y 5/00 | (2011.01) |
| B82Y 15/00 | (2011.01) |
| C12Q 1/6869 | (2018.01) |

(52) U.S. Cl.
CPC ..... *G01N 33/48721* (2013.01); *C12Q 1/6869* (2013.01); *B82Y 5/00* (2013.01); *B82Y 15/00* (2013.01)

(58) Field of Classification Search
CPC ........ B82Y 15/00; B82Y 5/00; C12Q 1/6825; C12Q 1/6869; C12Q 2565/607; C12Q 2565/631; G01N 33/48721
See application file for complete search history.

(56) References Cited

U.S. PATENT DOCUMENTS

| 2015/0218630 A1 | 8/2015 | Sun et al. |
| 2015/0284707 A1 | 10/2015 | Ferrara et al. |
| 2017/0037462 A1 | 2/2017 | Turner et al. |
| 2017/0044605 A1 | 2/2017 | Merriman et al. |

(Continued)

FOREIGN PATENT DOCUMENTS

| CA | 3137395 A1 | 7/2020 |
| CN | 104379761 A | 2/2015 |
| WO | 2017075620 A1 | 5/2017 |

OTHER PUBLICATIONS

Biswas, et al., "Universal Readers Based on Hydrogen Bonding or pi-pi Stacking for Identification of DNA Nucleotides in Electron Tunnel Junctions.", ACS Nano 2016, vol. 10, No. 12, pp. 11304-11316.

(Continued)

*Primary Examiner* — Kathryn Elizabeth Limbaugh
(74) *Attorney, Agent, or Firm* — Greenberg Traurig, LLP; Melissa Hunter-Ensor; Nathan Hsu

(57) ABSTRACT

This invention provides a system and related devices, methods, and molecular modules for electronically sequencing biopolymers.

18 Claims, 24 Drawing Sheets

Specification includes a Sequence Listing.

(56) References Cited

U.S. PATENT DOCUMENTS

| | | |
|---|---|---|
| 2018/0280968 A1 | 10/2018 | Qing et al. |
| 2018/0298436 A1 | 10/2018 | Lei et al. |
| 2018/0305727 A1 | 10/2018 | Merriman et al. |

OTHER PUBLICATIONS

Maity, et al., "A metal-free fluorescence turn-on molecular probe for detection of nucleoside triphosphates.", Chem Commun (Camb). 2016, vol. 53, No. 1, pp. 208-211.

International Search Report and Written Opinion in International Application No. PCT/US2019/063803 mailed Apr. 1, 2021.

Alvarez et al., "DNA/RNA transverse current sequencing: intrinsic structural noise from neighboring bases," Frontiers in Genetics, Jun. 2015, vol. 6, Article No. 213, pp. 1-11.

Amdursky, Nadav, "Electron Transfer across Helical Peptides," ChemPlusChem, 2015, vol. 80, pp. 1075-1095.

Armentano et al., "Self-Assembling of Cytosine Nucleoside into Triply-Bound Dimers in Acid Media. A Comprehensive Evaluation of Proton-Bound Pyrimidine Nucleosides by Electrospray Tandem Mass Spectrometry, X- rays Diffractometry, and Theoretical Calculations," Journal of the American Society for Mass Spectrometry, 2004, vol. 15, pp. 268-279.

Chen et al., "A protein transistor made of an antibody molecule and two gold nanoparticles," Nature Nanotechnology, Mar. 2012, vol. 7, pp. 197-203.

Deamer et al., "Three decades of nanopore sequencing," Nature Biotechnology, May 2016, vol. 34, No. 5, pp. 518-524.

Di Ventra et al., "Decoding DNA, RNA and peptides with quantum tunnelling," Nature Nanotechnology, Feb. 2016, vol. 11, pp. 117-126.

Fujii et al., "Rectifying Electron-Transport Properties through Stacks of Aromatic Molecules Inserted into a Self-Assembled Cage," Journal of the American Chemical Society, 2015, vol. 137, pp. 5939-5947.

Goodwin et al., "Coming of age: ten years of next-generation sequencing technologies", Nature Reviews Genetics, Jun. 2016, vol. 17, pp. 333-351.

Gordon et al., "Long-read sequence assembly of the gorilla genome," Science, Apr. 1, 2016, vol. 352, No. 6281, Article No. aae0344, pp. 1-8.

Ing et al., "Electronic Conductivity in Biomimetic α-Helical Peptide Nanofibers and Gels", American Chemical Society Nanotechnology, 2018, vol. 12, pp. 2652-2661.

Jain et al., "Improved data analysis for the MinION nanopore sequencer," Nature Methods, Apr. 2015, vol. 12, No. 4, pp. 351-356.

Kalyoncu et al., "Genetically encoded conductive protein nanofibers secreted by engineered cells," The Royal Society of Chemistry Advances, 2017, vol. 7, pp. 32543-32551.

Kitagawa et al., "Rigid Molecular Tripod with an Adamantane Framework and Thiol Legs. Synthesis and Observation of an Ordered Monolayer on Au(111)," The Journal of Organic Chemistry, 2006, vol. 71, pp. 1362-1369.

Lagerqvist et al., "Fast DNA Sequencing via Transverse Electronic Transport," Nano Letters, 2006, vol. 6, No. 4, pp. 779-782.

Laszlo et al., "Decoding long nanopore sequencing reads of natural DNA," Nature Biotechnology, Aug. 2014, vol. 32, No. 8, pp. 829-833.

Lee et al., "Rigid adamantane tripod linkage for well-defined conductance of a single-molecule junction," Physical Chemistry Chemical Physics, 2010, vol. 12, pp. 11763-11769.

Lindsay, Stuart, "The promises and challenges of solid-state single-molecule sequencing," Nature Nanotechnology, Feb. 2016, vol. 11, pp. 109-111.

Malak et al., "Long-Range Electron Transfer Across Peptide Bridges: The Transition from Electron Superexchange to Hopping," Journal of the American Chemical Society, 2004, vol. 126, pp. 13888-13889.

Manrao et al., "Reading DNA at single-nucleotide resolution with a mutant MspA nanopore and phi29 DNA polymerase," Nature Biotechnology, Apr. 2012, vol. 30, No. 4, pp. 349-353.

Meadows et al., "Boronic Acid Mediated Coupling of Catechols and N-Hydroxylamines: A Bioorthogonal Reaction to Label Peptides," Organic Letters, 2017, vol. 19, pp. 3179-3182.

Metzker, Michael L., "Emerging technologies in DNA sequencing," Genome Research, 2005, vol. 15, pp. 1767-1776.

Mfuh et al., "Scalable, Metal- and Additive-Free, Photoinduced Borylation of Haloarenes and Quaternary Arylammonium Salts," Journal of the American Chemical Society, 2016, vol. 138, pp. 2985-2988.

Morera et al., "Synthesis of 1,2-Dithiolane Analogues of Leucine for Potential Use in Peptide Chemistry," Organic Letters, 2002, vol. 4, No. 7, pp. 1139-1142.

Mukhopadhyay, Rajendrani, "DNA sequencers: the next generation," Analytical Chemistry, Mar. 1, 2009, vol. 81, No. 5, pp. 1736-1740.

Nakatsuka et al., "Aptamer-field-effect transistors overcome Debye length limitations for small-molecule sensing," Science, 2018, vol. 362, pp. 319-324.

Neubert et al., "Functionalization of gold and graphene electrodes by p-maleimido-phenyl towards thiol-sensing systems investigated by EQCM and IR ellipsometric spectroscopy," Applied Surface Science, 2017, vol. 421, pp. 755-760.

Ohsawa et al., "A Direct and Mild Formylation Method for Substituted Benzenes Utilizing Dichloromethyl Methyl Ether-Silver Trifluoromethanesulfonate," The Journal of Organic Chemistry, 2013, vol. 78, pp. 3438-3444.

Olsen et al., "Electronic Measurements of Single-Molecule Processing by DNA Polymerase I (Klenow Fragment)," Journal of the American Chemical Society, 2013, vol. 135, pp. 7855-7860.

Petrov et al., "Nonadiabatic donor-acceptor electron transfer mediated by a molecular bridge: A unified theoretical description of the superexchange and hopping mechanism," Journal of Chemical Physics, Oct. 15, 2001, vol. 115, No. 15, pp. 7107-7122.

Prasongkit et al., "Theoretical assessment of feasibility to sequence DNA through interlayer electronic tunneling transport at aligned nanopores in bilayer graphene," Scientific Reports, Dec. 4, 2015, vol. 5, Article No. 17560, pp. 1-9.

Pugliese et al., "Processive Incorporation of Deoxynucleoside Triphosphate Analogs by Single-Molecule DNA Polymerase I (Klenow Fragment) Nanocircuits," Journal of the American Chemical Society, 2015, vol. 137, pp. 9587-9594.

Raliski et al., "Site-Specific Protein Immobilization Using Unnatural Amino Acids," Bioconjugate Chemistry, 2014, vol. 25, pp. 1916-1920.

Reguera et al., "Extracellular electron transfer via microbial nanowires," Nature, Jun. 23, 2005, vol. 435, pp. 1098-1101.

Reinus et al., "A Copper-Catalyzed N-Alkynylation Route to 2-Substituted N-Alkynyl Pyrroles and Their Cyclization vol. 49, into Pyrrolo[2,1-c]oxazin-1-ones: A Formal Total Synthesis of Peramine," Synthesis, 2017, vol. 49, pp. 2544-2554.

Rhoads et al., "PacBio Sequencing and Its Applications," Genomics Proteomics Bioinformatics, 2015, vol. 13. pp. 278-289.

Sadar et al., "Confined Electrochemical Deposition in Sub-15 nm Space for Preparing Nanogap Electrodes," ECS Transactions, 2017, vol. 77, No. 7, pp. 65-72.

Staderini et al., "A tripod anchor offers improved robustness of peptide-based electrochemical biosensors," Sensors and Actuators B: Chemical, 2018, vol. 274, pp. 662-667.

Tong et al., "Oxygen evolution at functionalized carbon surfaces: a strategy for immobilization of molecular water oxidation catalysts," Chemical Communications, 2012, vol. 48, pp. 10025-10027.

Treangen et al., "Repetitive DNA and next-generation sequencing: computational challenges and solutions," Nature Reviews Genetics, Jan. 2012, vol. 13, pp. 36-46.

Tsutsui et al., "Identifying single nucleotides by tunnelling current," Nature Nanotechnology, Apr. 2010, vol. 5, pp. 286-290.

Tsutsui et al., "Single-molecule sensing electrode embedded in-plane nanopore," Scientific Reports, Jul. 28, 2011, vol. 1, No. 46, pp. 1-6.

(56) References Cited

OTHER PUBLICATIONS

Wang et al., "Effects of Metal-Molecule Contact and Molecular Structure on Molecular Electronic Conduction in Nonresonant Tunneling Regime: Alkyl versus Conjugated Molecules," The Journal of Physical Chemistry C, Jul. 2008, vol. 112, pp. 13010-13016.
Xie et al., "Local electrical potential detection of DNA by nanowire-nanopore sensors," Nature Nanotechnology, Feb. 2012, vol. 7, pp. 119-125.
Xin et al., "Stereoelectronic Effect-Induced Conductance Switching in Aromatic Chain Single-Molecule Junctions," Nano Letters, 2017, vol. 17, pp. 856-861.
Office Action dated Nov. 28, 2023 in corresponding Chinese Patent Application No. 201980090825.8 (11 pages).
English translation of Office Action dated Nov. 28, 2023 in corresponding Chinese Patent Application No. 201980090825.8 (15 pages).

N², N⁶-bis(naphthalen-2-ylmethyl)pyridine-2,6-dicarboxamide

Sequence: NH₂-ELKAIAQEFKAIAKEFKAIAFEFKAIAKQK

N³-(anthracen-2-ylmethyl)-N⁴-((5-carbamoyl-1H-1,2,4-triazol-3-yl)methyl)-1H-pyrrole-3,4-dicarboxamide

Reagents and reaction conditions: (*i*) bromoethynyltriisopropylsilane, 4,7-dimethoxy-1,10-phenanthroline, $Cu_2SO_4 \cdot 5H_2O$, $K_2CO_3$, $\Delta$; (*ii*) LiOH in $H_2O$ and TNF; (*iii*) 2-(aminomethyl)anthracene, DCC; (*iv*) 5-(aminomethyl)-4H-1,2,4-triazole-3-carboxamide, DCC; (*v*) tetra-n-butylammonium fluoride (TBAF).

Reagents and reaction conditions: (*i*) bromoethynyltriisopropylsilane, CuI, Pd(PPh₃)₄, *i*-Pr₂NH; ¹Δ; (*ii*) LiOH in H₂O and TNF; (*iii*) 2-(aminomethyl)anthracene, DCC; (*iv*) 5-(aminomethyl)-4H-1,2,4-triazole-3-carboxamide, DCC; (*v*) tetra-*n*-butylammonium fluoride (TBAF).

Sequence: NH$_2$-tyr-tyr-arg-lys-tyr-lys-glu-tyr-lys-tyr-asp-asp-tyr

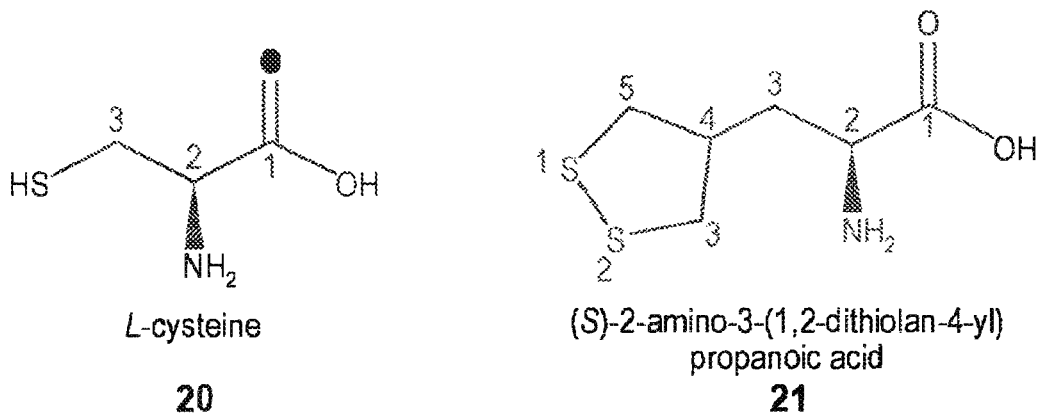
Fig. 14
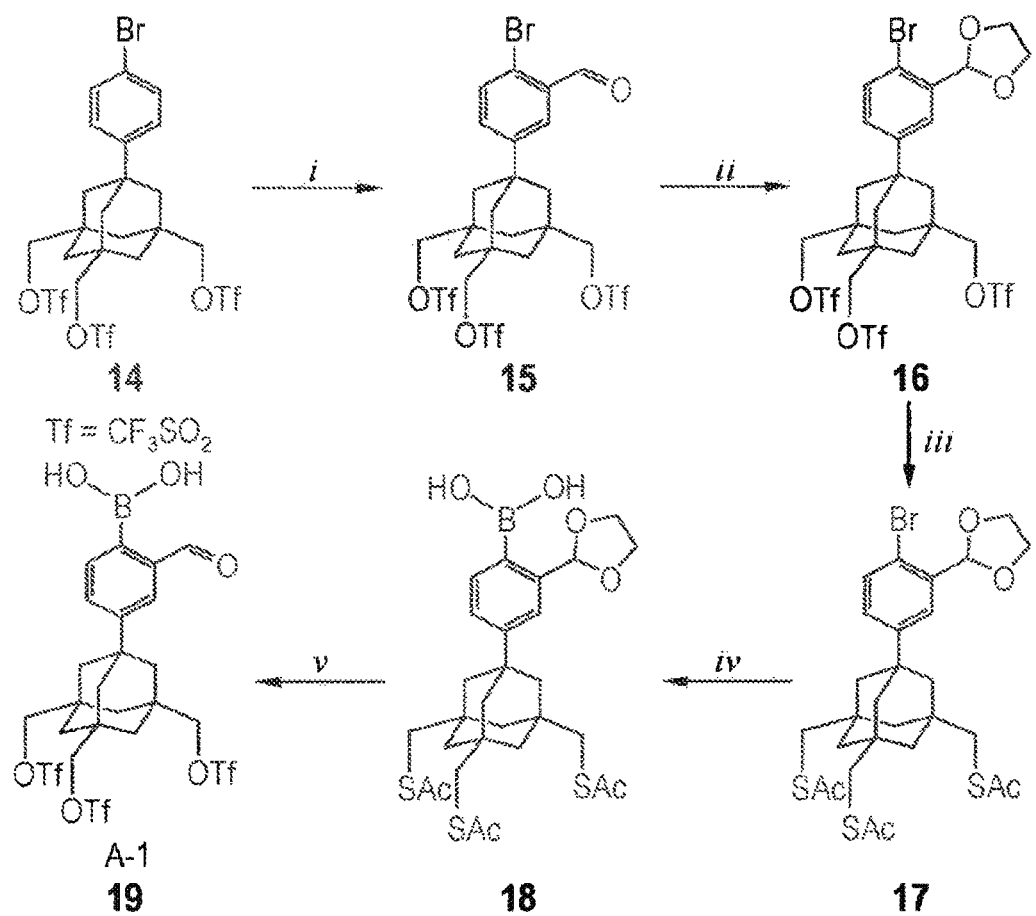
Reagents and reaction conditions: (*i*) Cl$_2$CHOMe, AgOTf; (*ii*) HC(OMe)$_3$, MeOH, p-toluenesulfonic acid; (*iii*) potassium thioacetate, 18-crown-6, DMF, Δ; (*iv*) B$_2$(OH)$_4$, hv, methanol; (*v*), p-toluenesulfonic acid.

SEQUENCE LISTING

<160> NUMBER OF SEQ ID NOS: 2

<210> SEQ ID NO 1
<211> LENGTH: 30
<212> TYPE: PRT
<213> ORGANISM: Artificial Sequence
<220> FEATURE:

```
<223> OTHER INFORMATION: Peptide

<400> SEQUENCE: 1

Glu Leu Lys Ala Ile Ala Gln Glu Phe Lys Ala Ile Ala Lys Glu Phe
1               5                   10                  15

Lys Ala Ile Ala Phe Glu Phe Lys Ala Ile Ala Lys Gln Lys
            20                  25                  30

<210> SEQ ID NO 2
<211> LENGTH: 11
<212> TYPE: PRT
<213> ORGANISM: Artificial Sequence
<220> FEATURE:
<223> OTHER INFORMATION: Peptide

<400> SEQUENCE: 2

Tyr Tyr Arg Lys Tyr Lys Glu Tyr Asp Asp Tyr
1               5                   10
```

SYSTEM FOR SEQUENCING BIOPOLYMERS

CROSS REFERENCE TO RELATED APPLICATIONS

This application is a U.S. National Phase application under 35 U.S.C. 371 of International Application No. PCT/US2019/063803 filed Nov. 27, 2019, which claims priority to and the benefit of U.S. Provisional application No. 62/772,837, filed Nov. 29, 2018, the contents of each of which are hereby incorporated herein by reference in their entirety.

FIELD OF INVENTION

Embodiments of the present invention are related to systems, methods, devices, and compositions of matter for identification and sequencing of biopolymers utilizing electronic measurements. More specifically, this disclosure includes embodiments where molecular clefts or tweezers are designed, synthesized, and functionalized with molecular wires bearing the bonding functions that bridge nanogaps, enabling one to identify biopolymers electronically based on their constituents at a single-molecule level.

BACKGROUND OF THE INVENTION

Next-generation sequencing (NGS) has reduced the cost and time of sequencing an individual human genome. However, NGS reads DNA sequences much shorter[2] than classical Sanger sequencing (~800 base read length on average).[3] One of the disadvantages is that the short reads cannot encapsulate long blocks of repetitive sequences, resulting in fragmented assemblies of the human genome where half of the sequences are composed of repeats with the size from 1 base (mononucleotide repeat or homopolymer) or 2 bases (dinucleotide repeat) to millions of bases, and the copy number from two to millions.[4] Single molecule real-time (SMRT) sequencing—referred to as a third-generation sequencing (developed by Pacific Biosciences)—offers sequences with an average read length of >10 kbp,[5] allowing for de novo assembly of large genomes such as gorilla's.[6] However, SMRT sequencing has a much higher error rate (~15%). Although the error can be overcome by high sequencing coverage (>30x), it will cost around $10,000 for a 30x human genome. For the use in clinics, ideally, the sequencing cost should be in a $100 per genome ballpark.[7]

Nanopore sequencing is a technology based on measuring ionic currents, which was conceptualized three decades ago.[8] A nanopore is an orifice with a diameter of nanometers, allowing a flow of fluids to conduct ions under voltage bias. When a single-stranded DNA—a polyanionic molecule—is electrophoretically translocated through the nanopore embedded in a thin membrane that separates two chambers filled with conductive electrolytes, it causes transiently blockages of ionic current. Since the nucleobases have distinguishable sizes, the blockage varies as the translocation proceeds. So the DNA sequence can be deduced from fluctuations of the ionic current. A commercial product MinION sequencer (www.nanoporetech.com) has been developed based on protein nanopores. Since there is no theoretical limit on a length of DNA for the translocation, the nanopore sequencing may be an ultimate tool for de novo sequencing and analysis of structural variations, overcoming those issues related to NGS's short reads in genomic assembly, which would be benefited from long reading. However, the protein nanopore can only achieve a low sequencing accuracy (85% with a single read[9]). Gundlach and coworkers have demonstrated that the current blockage in a protein nanopore composed of *Mycobacterium smegmatis* porin A (known as MspA) is a collected event of four nucleotides (quadromer), and therefore there are $4^4$ (i.e. 256) possible quadromers that exert a significant number of redundant current levels.[10, 11] Because the ionic current is affected by nucleotides beyond those inside the nanopore,[12] the notion of an atomically thin nanopore for sequencing may not be conceivable to achieve a single nucleotide resolution.

Ventra et al. proposed to sequence DNA using a pair of electrodes separated by a distance of nanometers[13] and electrons can tunnel through such a nanogap. Since then, much progress has been made in reading nucleobases by the electron tunneling.[14] With the tunneling nanogap embedded in a solid-state nanopore, single-stranded DNA can be sequenced by translocating its nucleotides through the gap sequentially. Given that the tunneling current is highly sensitive to changes in the distance (~ an order of magnitude per Å), the tunneling measurement provides a highly spatial resolved method for sequencing DNA and may achieve a single nucleotide resolution since the distance between two adjacent bases in a single stranded DNA is greater than 3.4 Å. However, it requires a sharp electrode to achieve the single base resolution. It has been demonstrated that nucleoside monophosphates and oligonucleotides can generate tunneling currents in a small nanogap (<1 nm), but the signals overlap one another among the naturally occurring DNA nucleotides,[15, 16] verified by theoretic calculation.[17, 18] Although the tunneling measurement was performed at a gap distance of ~2.5 nm by functionalizing the two electrodes with recognition molecules,[19] the manufacture of <3 nm tunneling gaps is technically challenging at present.

Collins and coworkers invented a single-wall carbon nanotube (SWCNT) field-effect transistor (FET) device with a Klenow fragment of DNA polymerase I tethered on it to monitor its DNA synthesis.[20, 21] In the device, when a nucleotide was incorporated into a DNA strand, a brief excursion of $\Delta I(t)$ below the mean baseline currents was recorded. The incorporation of different nucleotides by the enzyme results in differences in $\Delta I$. This technology can potentially be used in sequencing DNA. The carbon nanotube is a material made from just a single layer of carbon atoms locked in a hexagonal grid. It is a rigid chemical structure. Its sensing may rely on electrostatic gating motions of charged side chains close to the protein attachment site.

It has been reported that a silicon nanowire built on the edge of a SiN nanopore can detect DNA translocation by sensing the changes in electrical potential.[22] Also, a field-effect transistor (FET) can sense conformational changes in proximity to semiconductor channels gated conductance in physiological buffers, resulting in the highly sensitive detection of ligand and receptor interactions.[23] However, these FET devices have not exhibited a capacity to read single DNA bases in a DNA strand.

A nanojunction can be formed by connecting a molecular wire to two electrodes separated by a nanoscale gap. It allows electrons to flow when integrated into an electrical circuit. In general, the molecular component is covalently attached to the electrodes, and the electronic conduction of a junction is affected by the molecular structure and molecule-metal contact.[24] However, its electronic state can be switched by stereoelectronic effect[25] and altered by external stimuli. For example, the conductance of a host-guest molecular junction can be tuned by the insertion of guest molecules.[26] Also, a protein transistor can be fabricated by bridging a nanogap using an antigold nanoparticle antibody.[27]

Electron transfer (ET) an be mediated along with proteins and peptides.[28, 29] Arguably, ET through peptides may operate through tunneling and hopping in parallel; however, their contributions change with the length of the mediating bridge. For short bridges, tunneling is dominating, whereas for long bridges, hopping becomes more pronounced,[36] which was demonstrated experimentally by Isied and coworkers.[31] The composition of the side chains, hydrogen bonds, and an α-helical secondary structure have been identified as important factors contributing to the hopping and tunneling conductivity in these peptide systems over short distances. Thus, the charge transfer properties of peptides can be modulated by manipulating their secondary structure.

This invention provides a system equipped by nanodevices to sequence biopolymers. One of them is a nanogap composed of nanoelectrodes. For sequencing biopolymers, the nanogap is bridged by a wired entity that can capture individual monomers in a polymeric strand by forming noncovalent complexes resulting in changes of structures and subsequently conductance of the wire. Since each complex is different from one another, it exerts a different effect on the conductance. The current fluctuations can be used to identify the individual monomers in a polymeric sequence.

BRIEF DESCRIPTION OF THE DRAWINGS

FIG. 6 (continued) shows a route to synthesizing a molecular cleft bearing an ethynyl group (MC-1).

FIG. 14 shows the chemical structures of reagents used to functionalize the termini of peptide wires for their attachment to metal electrodes.

FIG. 14 also shows a route to synthesizing a tripod anchor for attaching peptides to metal surfaces.

SUMMARY OF THE INVENTION

This invention provides a system comprising a nanojunction that can sense chemical entities for electronically sequencing biopolymers, such as DNA and RNA, a nanopore (or a nanochannel) for transporting individual biopolymers to the sensing device, the movement of which is controlled by a mechanical device. This invention also provides molecular probes that are attached to molecular wires for the identification of individual chemical entities in a sample molecule. The same system, devices, and methods apply to sequence proteins, peptides, polysaccharides, etc. Herein, the disclosure demonstrates the design, fabrication, and use of this type of device for sequencing DNA.

Figure 1:
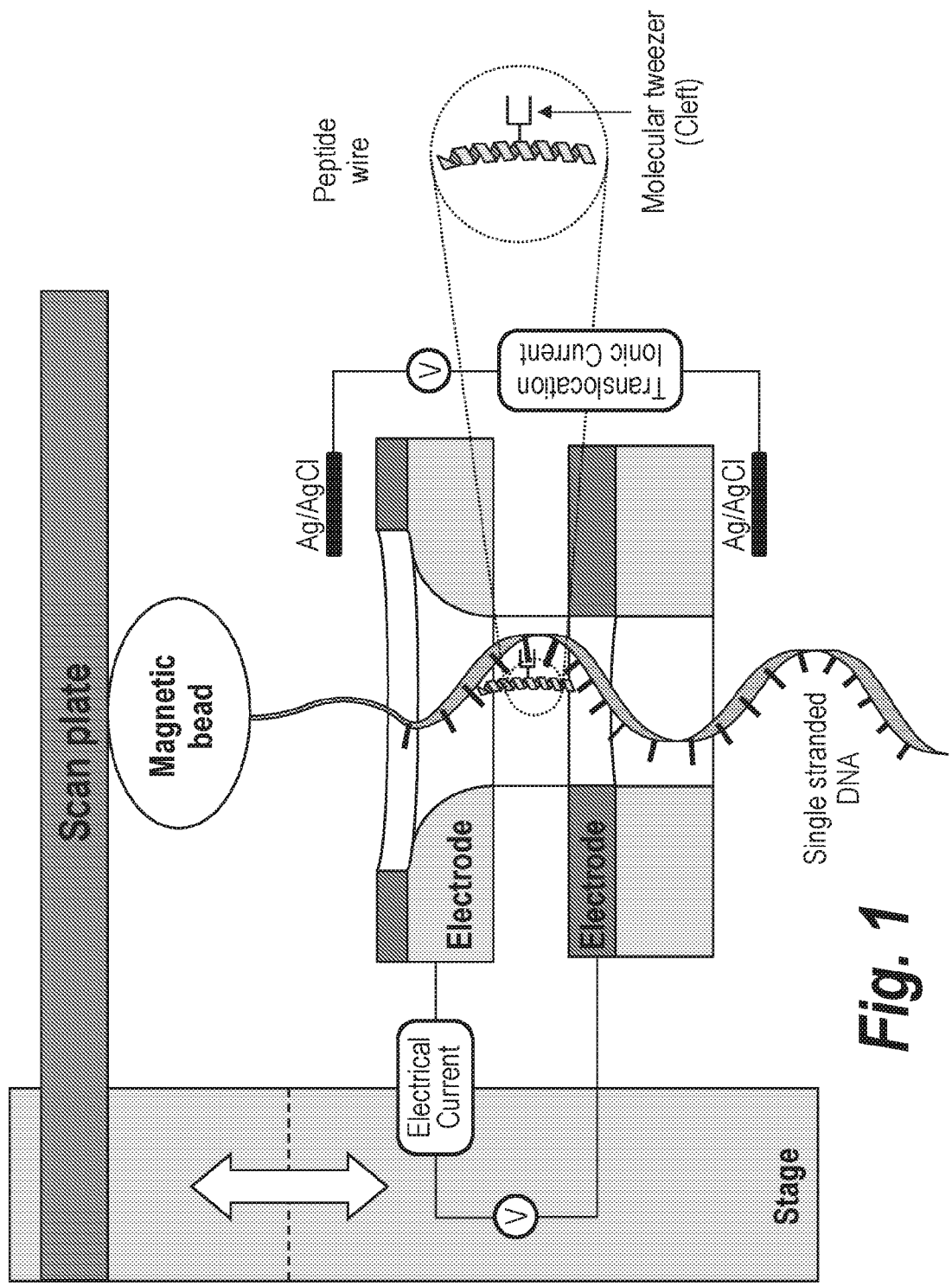
FIG. 1 shows a schematic drawing of a molecular tweezer-nanopore system for sequencing DNA in accordance with various embodiments.

In one embodiment of the invention (FIG. 1), the said system comprises: (a) a nanopore embedded in a membrane that separates two fluidic reservoirs, allowing the said biopolymers to translocate from one side to the other side; preferred diameters of the nanopore are those between 2 nm to 1 μm; the more preferred diameters are those between 3 nm to 40 nm, and the most preferred is the one between 3 nm to 10 nm; (b) a pair of stacked electrodes separated by a dielectric layer, which is located in the interior of the nanopore; the preferred thicknesses for the dielectric layer are those between 3 nm and 100 nm, the more preferred thicknesses are those between 4 nm and 40 nm, and the most preferred thickness is the one between 4 nm to 10 nm; The pair of electrodes are made of the same material or different materials. Also, multiple pairs of electrodes are built in the nanopore, so a biopolymer would be sequenced multiple times when it passes through the nanopore device. (c) a wired molecular module that can interact with individual constituents of the said biopolymers through noncovalent bonding, which bears two anchoring sites for bonding to the paired electrodes covalently; Under a voltage bias, the said molecular module allows for electrons transport from one electrode to the other electrode; (d) a mechanism to control the translocation velocities of the said polymeric molecules through nanopores to increase the measuring accuracies. The movement control mechanism can be an enzyme, such as a polymerase or a helicase, in combination with viscous media and/or some electrophoretic force, or a nanometer precision piezo drive or any electromechanical drives and can be controlled by an adjustable magnet, or a combination of all above. The embodiment demonstrates that when a single-stranded DNA is translocated through the nanopore, its movement is controlled using a piezo drive described in our previous invention with sub-nanometer resolution (described in PCT WO2017075620A1). For sequencing DNA, a preferred speed is the one between 5 ms (millisecond) to 20 ms per base; the second preferred speed between 1 ms to 100 ms per base, and the less preferred speed between 0.1 ms to 1000 ms per base.

Figure 2:
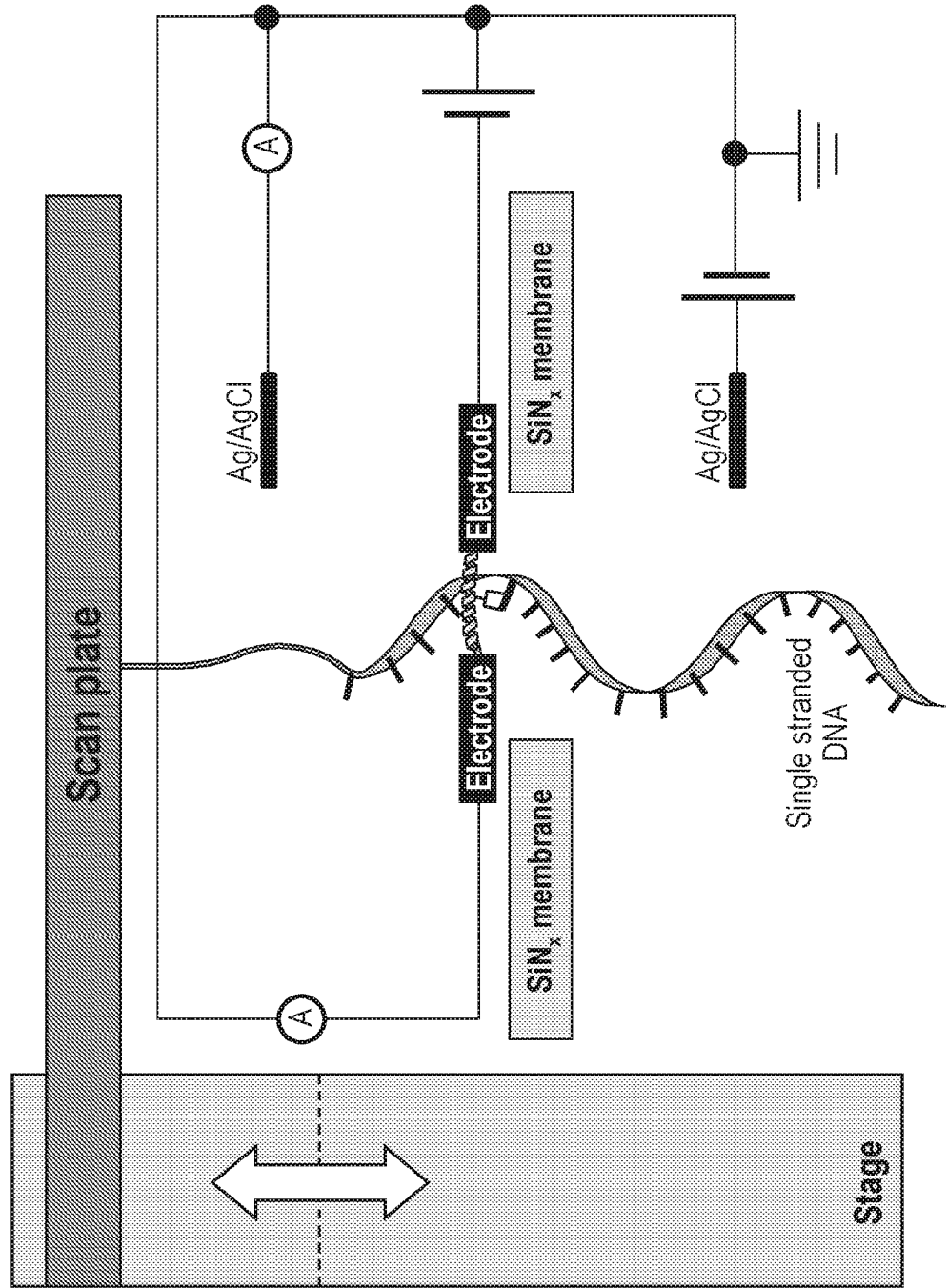
FIG. 2 shows a schematic drawing of the system with its paired electrodes in a planar configuration.

In another embodiment, instead of being stacked in the nanopore, the paired electrodes are fabricated on the top surface of the nanopore either at its trans or cis exit (FIG. 2). Thus, the resultant planar nanogap between the two electrodes is made over the center of the nanopore, off the center, or along the edge of the nanopore. The preferred diameters for the nanogap are those between 2 nm to 40 nm and the most preferred diameter is the one between 4 nm to 10 nm. The planar nanogap can be fabricated electrochemically with a feedback control over the nanopore.[32, 33]

In yet another embodiment of the invention, the paired electrodes are transversely fabricated in a nanochannel and functionalized with the said molecular modules. A polymeric molecule, such as DNA, flows into the nanochannel and subsequently passes through the nanogap where its sequence is readout. The DNA movement is controlled by an enzyme, such as a polymerase or a helicase, in combination with viscous media and/or some electrophoretic force, or by a precise piezo drive or a precise electromechanical drive, by an adjustable magnet, by an electrophoretic force in combination with viscous media, or by microfeatures in the microchannel, such as micropillars (posts), porous media, etc., which stretch DNA and slow down its movement.

In some embodiment of the invention, the said biopolymer (such as DNA) is attached to a bead so that it can be stopped at an entrance of the nanopore or nanochannel near to the nanogap as it passes through the gap and then is pulled away from the nanogap in a precisely controlled manner so that its constituents can be identified by the wired molecular probe as it moves through the gap.

Figure 3A:
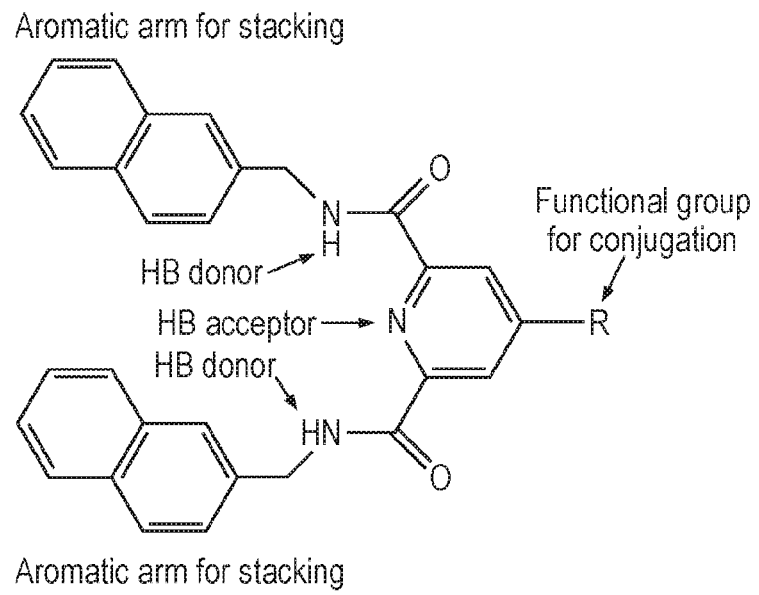
FIG. 3 shows the chemical structure of a molecular cleft (a) and its DFT (density functional theory) model (b).
Figure 3B:
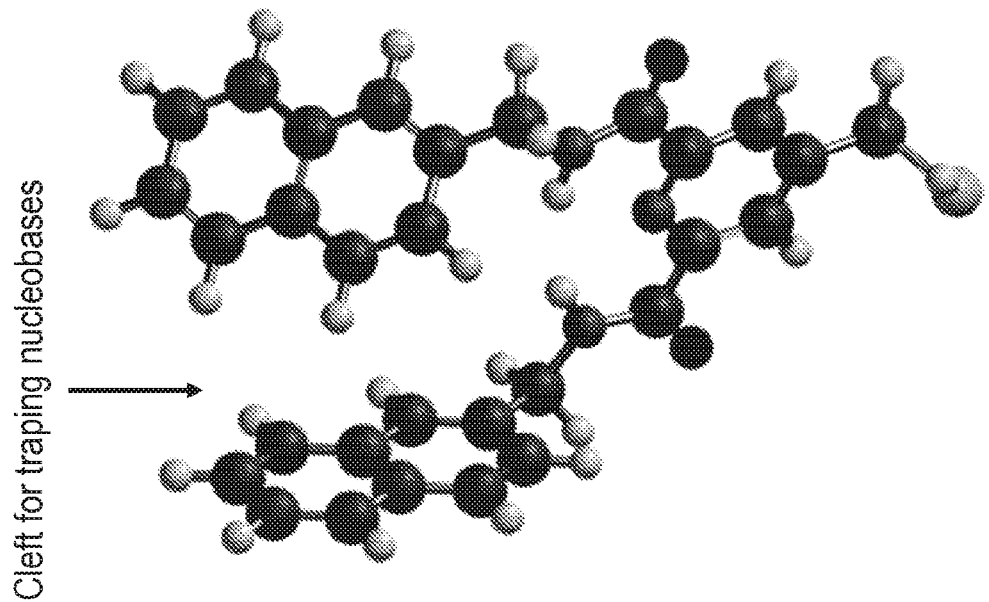

In some embodiment of the invention, a molecular cleft is designed and synthesized as a molecular probe to recognize the nucleobases for sequencing nucleic acids, which is composed of two aromatic motifs connected to a pyridine platform (FIG. 3).

Figure 4:
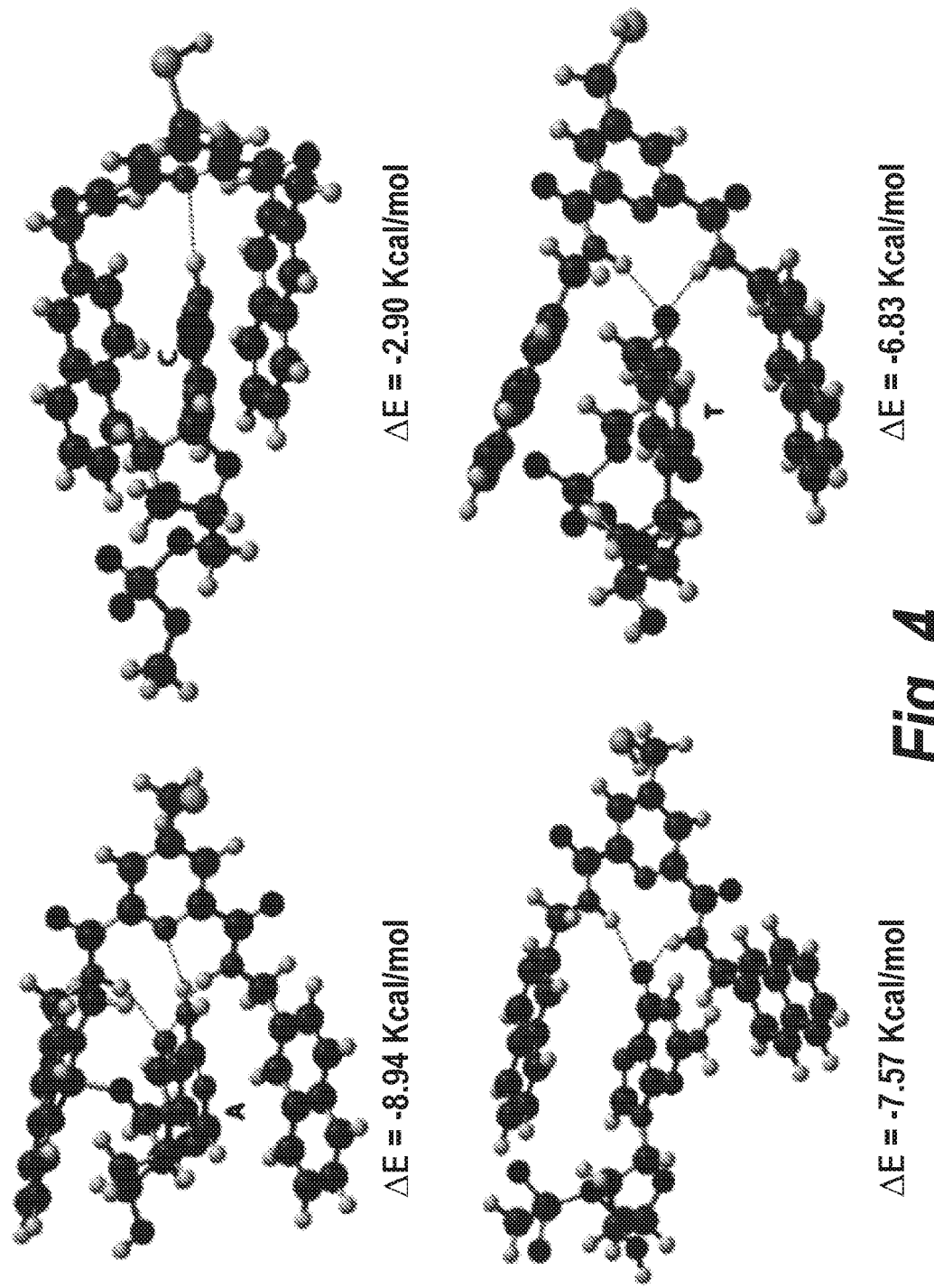
FIG. 4 shows DFT structures of the cleft complexes with DNA nucleotides and their binding energies.

In one embodiment, the molecular cleft forms complexes with DNA nucleobases, respectively, by trapping them in the hollow space through both hydrogen bonding and stacking interactions. These complexes have distinct structures and different binding energies, which can be used as signatures to identify individual nucleobases (FIG. 4).

Figure 5:
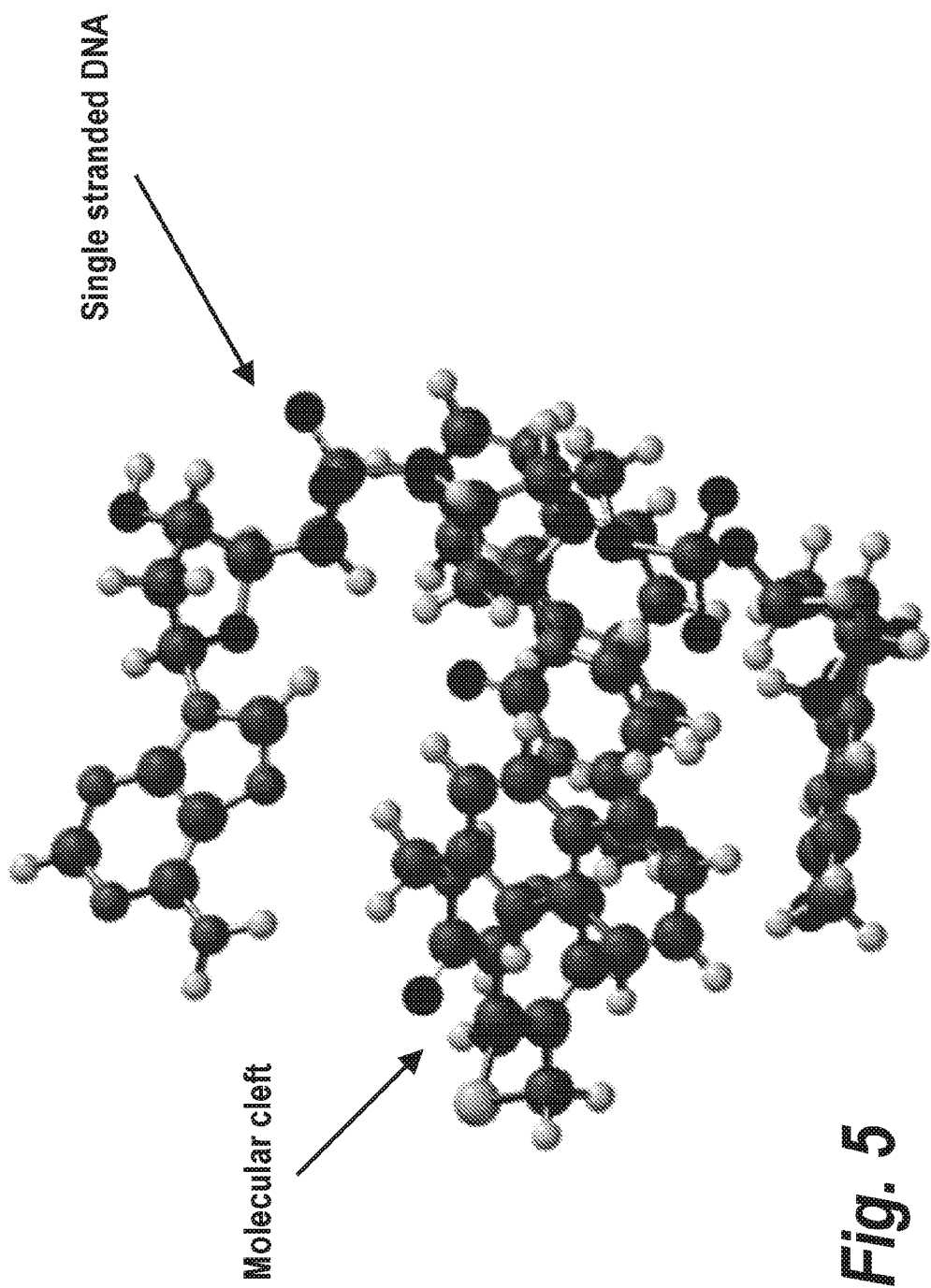
FIG. 5 shows a complex of the molecular cleft with a nucleobase in a single-stranded DNA fragment.

In another embodiment, the molecular cleft can form a complex with an individual nucleobase in a single-stranded DNA by trapping it in the hollow space (FIG. 5).

One embodiment of the invention provides a method to synthesize the said molecular cleft containing an ethynyl function (MC-1) for its conjugation with molecular wires (Scheme 1).

In some embodiments, peptides are used as a conductive molecular wire to bridge the electrodes. Thus, a peptide molecular junction coupled with the said molecular cleft is used as a sensing component. When a nucleobase is bound to the molecular cleft, it disturbs the conformation of the peptide molecule, sequentially resulting in the change of its conductance. Each nucleobase has different impacts on the peptide wire's conductance differently so that we can identify them by measuring the current flows.

Figure 6:
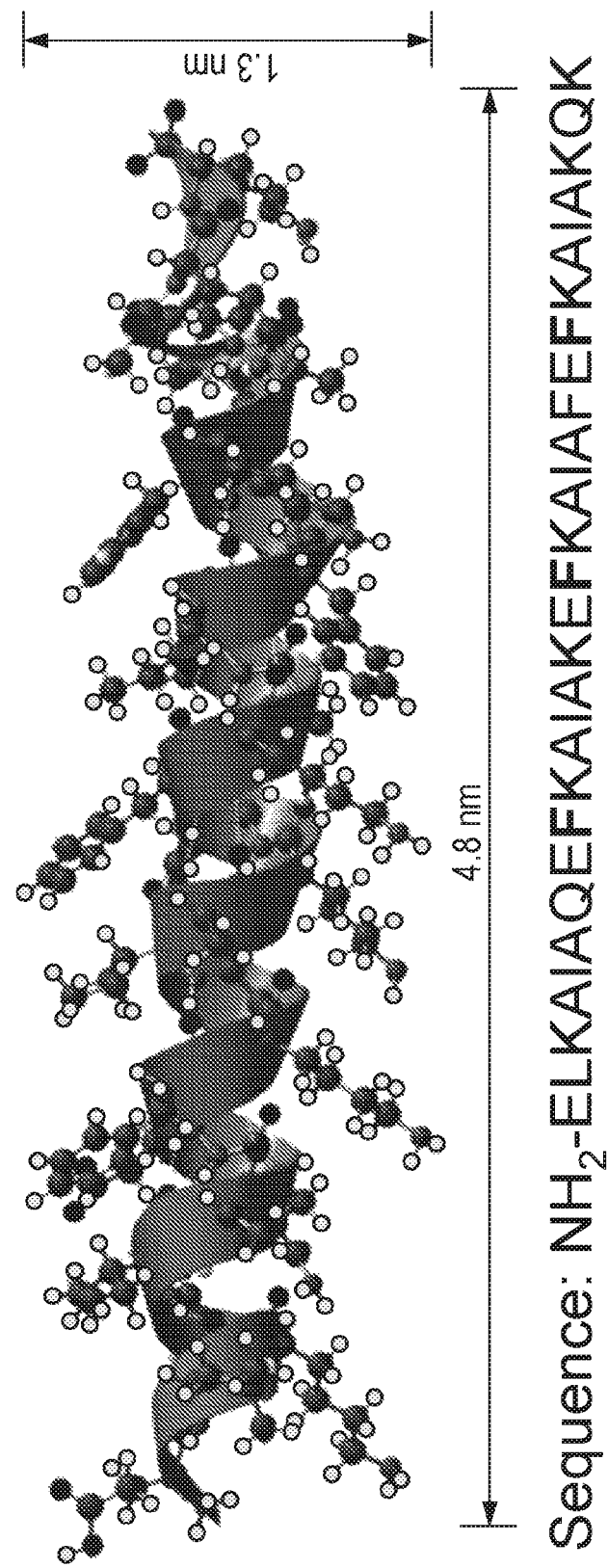
FIG. 6 shows a peptide wire with an α helical structure.
Figure 6:
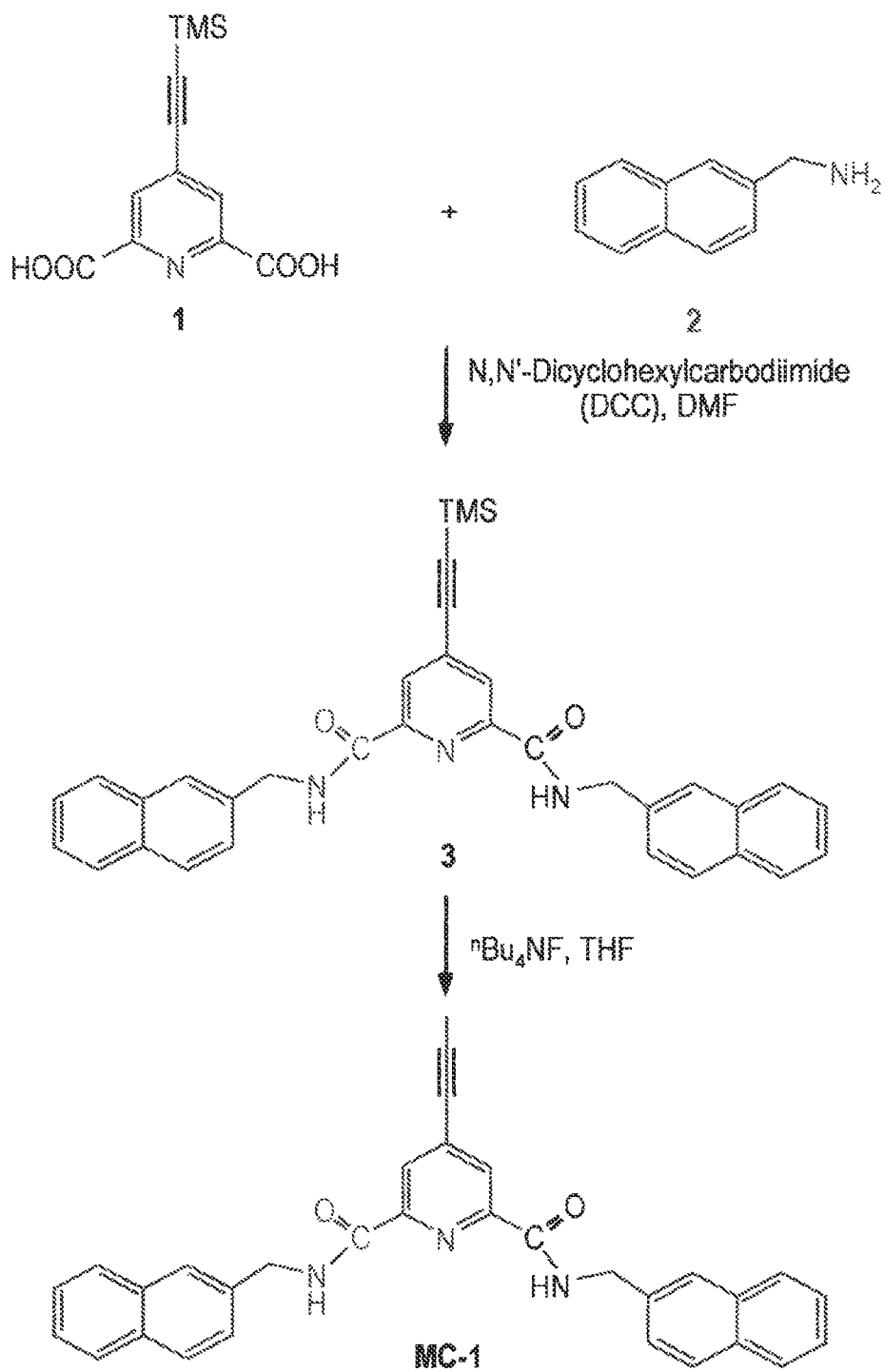

In one embodiment, the molecular wire is a peptide that has an α-helix structure with a sequence of NH$_2$-ELKA-IAQEFKAIAKEFKAIAFEFKAIAKQK that contains aromatic and charged amino acid residues (FIG. 6). The peptide wire is conductive.[34]

Figure 7:
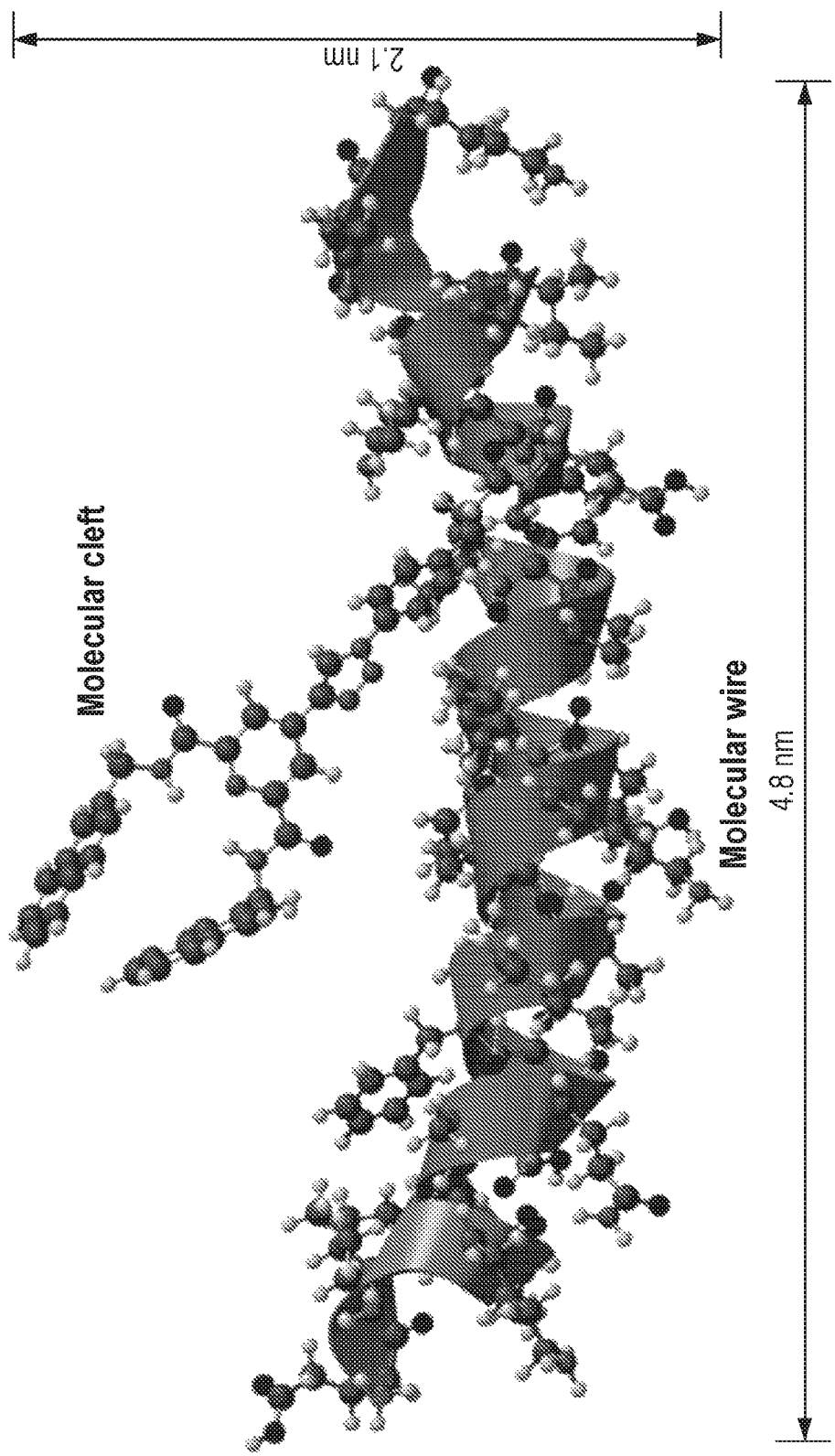
FIG. 7 shows a three-dimensional structure of a molecular cleft-peptide conjugate calculated by molecular mechanics.

In one embodiment, the invention provides a conjugate of the peptide wire with the molecular cleft, which displays as a T-shaped molecule. First, the peptide is modified with one of its phenylalanines replaced by azidophenylalanine. Thus, the molecular cleft, for example, MC-1, reacts with the modified peptide in the presence of a copper catalyst to form a molecular module with one peptide conjugated to one molecular cleft (FIG. 7).[35]

In some embodiments, a molecular cleft is composed of two different aromatic motifs, one for the π-π interaction and another one for hydrogen bonding with nucleobases, which are connected to a five-membered aromatic ring, referred to as a molecular tweezer.

Figure 8A:
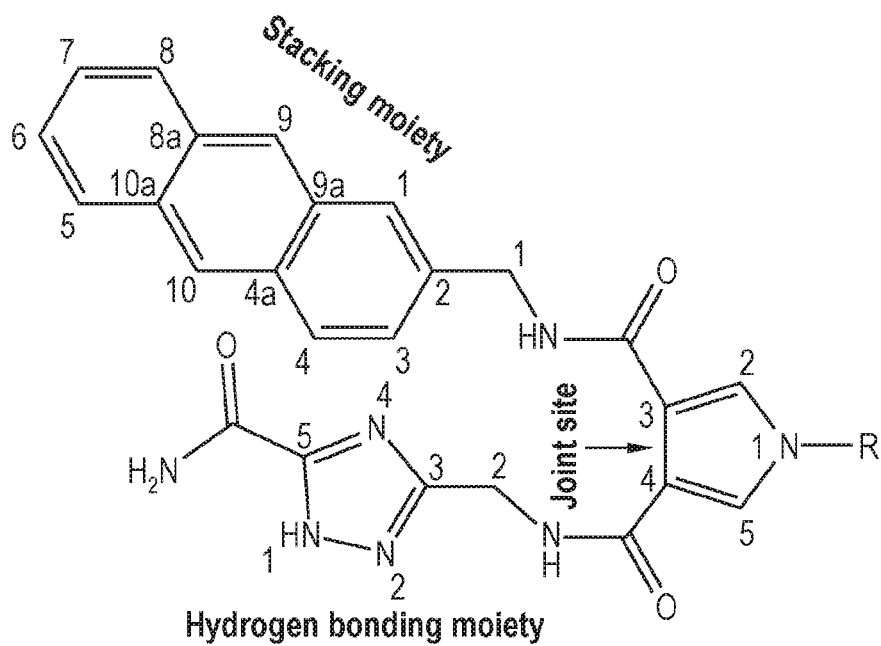
FIG. 8 shows the chemical structure of a molecular tweezer (a) and its DFT model (b).
FIG. 8(c) shows a route to synthesizing a molecular tweezer bearing an ethynyl group (MT-1).
Figure 8B:
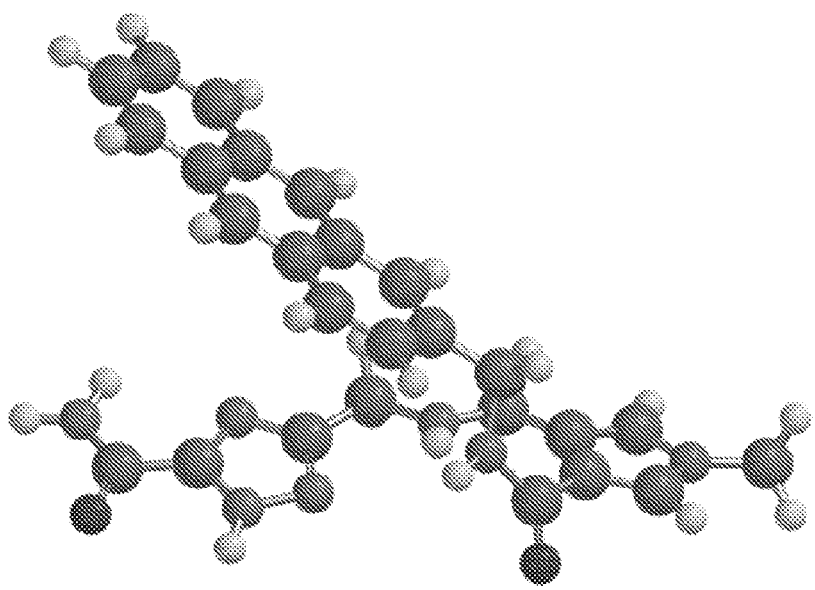
Figure 8C:
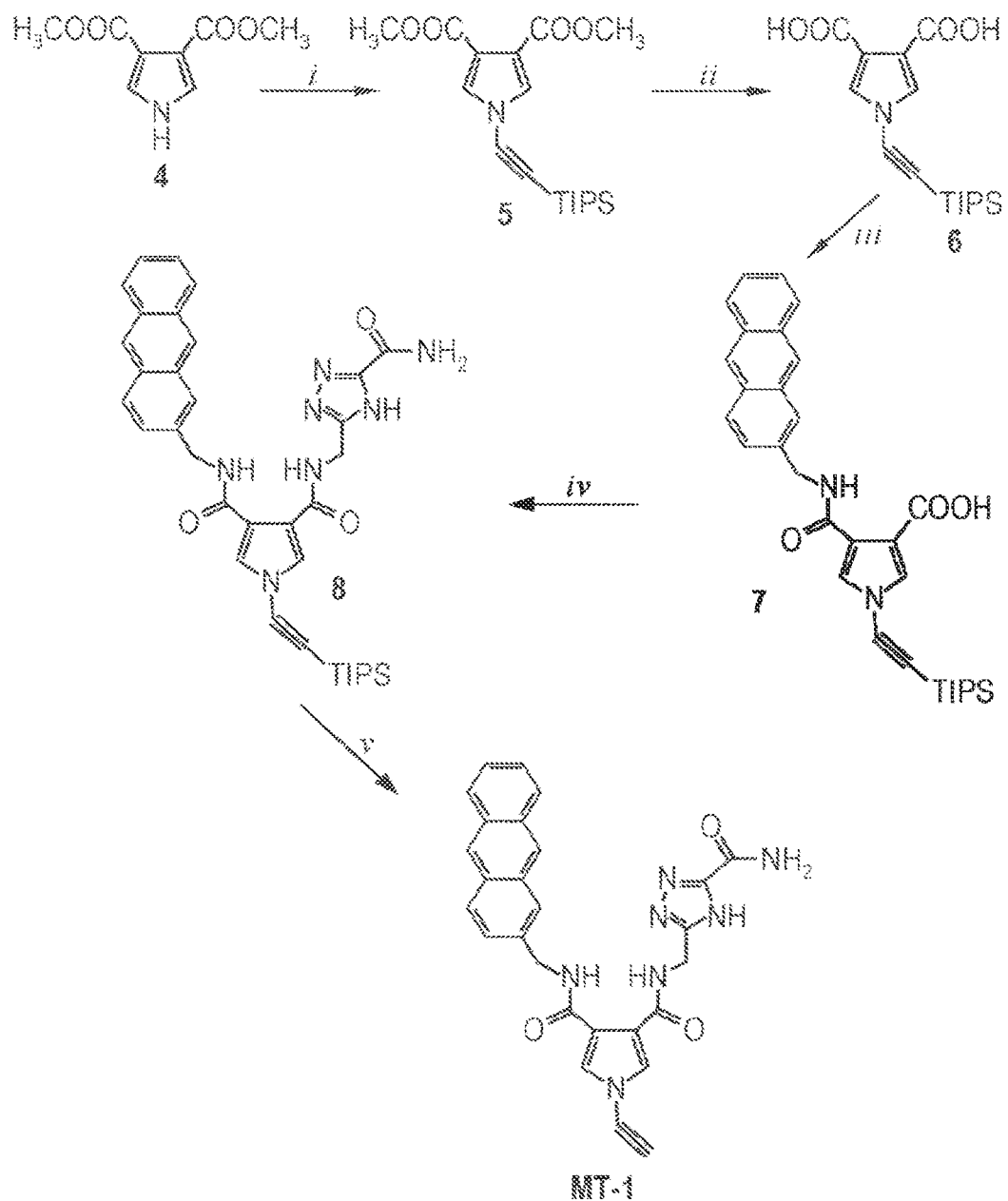
Figure 9A:
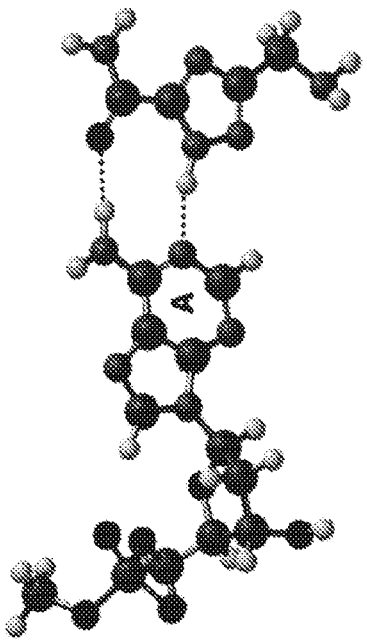
FIG. 9 shows DFT structures of the complexes of both molecular tweezer and hydrogen bonding moiety with DNA nucleotides and their bonding energies calculated by DFT calculation.
Figure 9A:
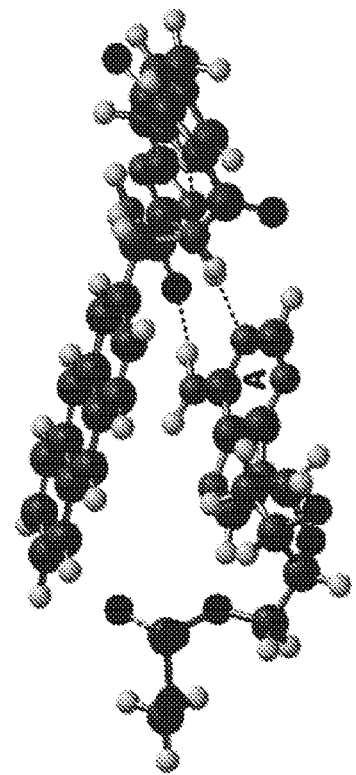
Figure 9B:
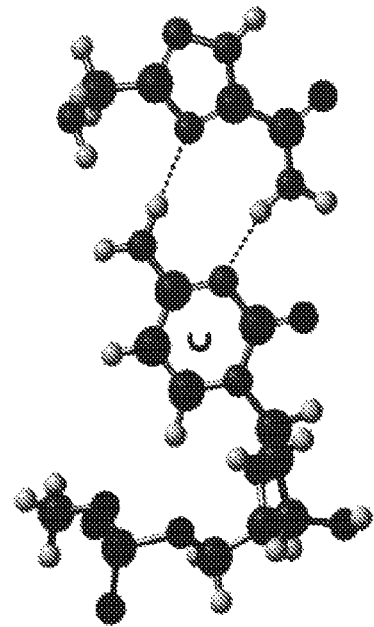
Figure 9B:
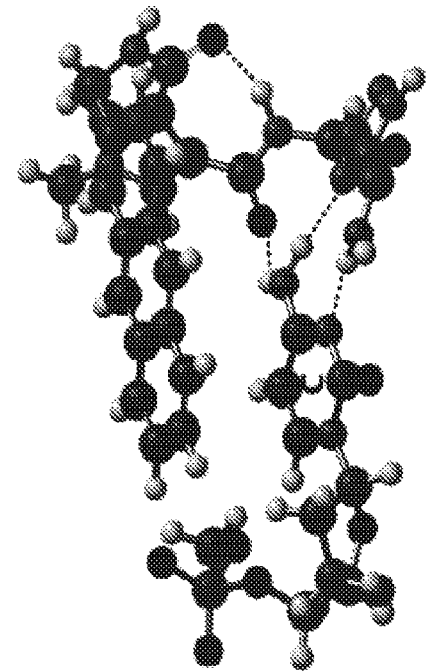
Figure 9C:
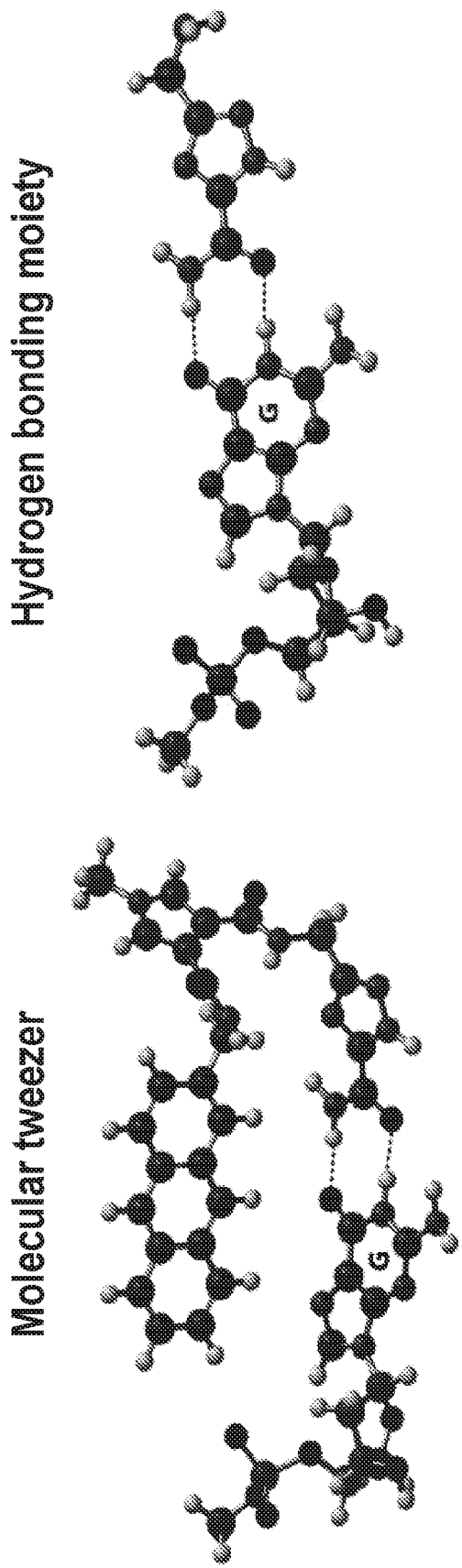
Figure 9D:
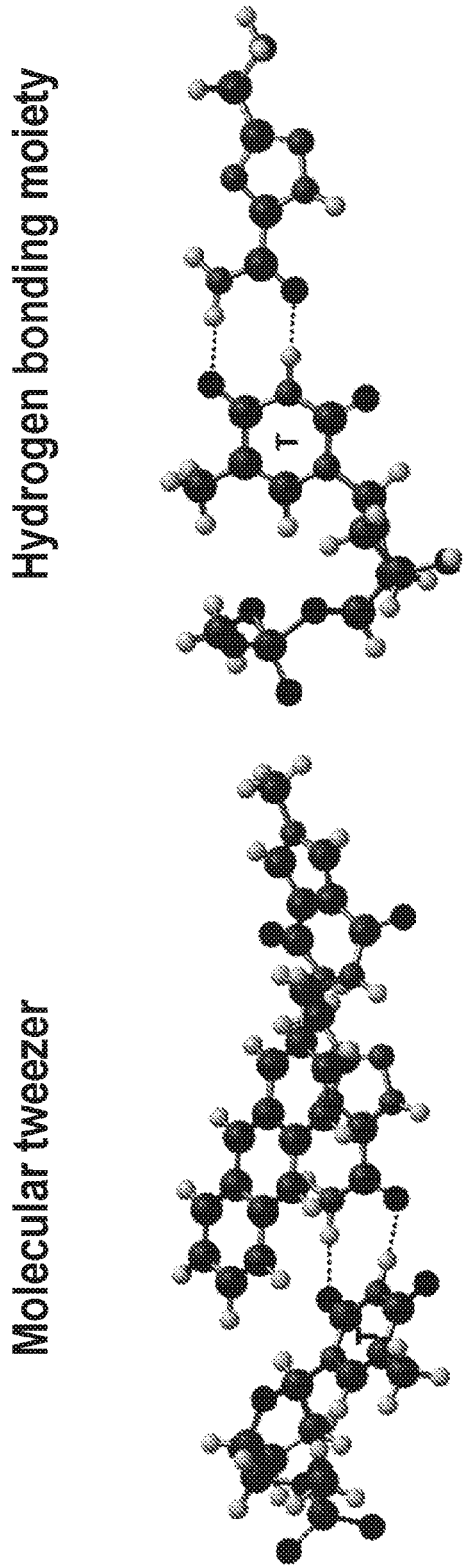

In one embodiment, the molecular tweezer is a molecule that is composed of one hydrogen bonding moiety, triazole carboxamide, and one aromatic stacking moiety anthracene connected through a pyrrole structure (FIG. 8a). The DFT model shows that the molecular has a tweezer shape (FIG. 8b).

In one embodiment, the invention provides a method to synthesize a molecular tweezer containing an ethynyl function for forming a conjugate with the said peptide wire (Scheme 2, MT-1).

The molecular tweezer closes when it interacts with nucleobases. DFT calculation shows that it forms complexes with nucleobase by the hydrogen bonding horizontally and π-π stacking vertically (FIG. 9). The interactions between the molecular tweezer and nucleobases form noncovalent complexes with different structures, resulting in distinguishable binding energies. These characteristics can be used to identify the nucleobases. By comparison, the molecular tweezer forms more stable complexes with DNA nucleotides than the hydrogen bonding moiety alone.

Figure 10A:
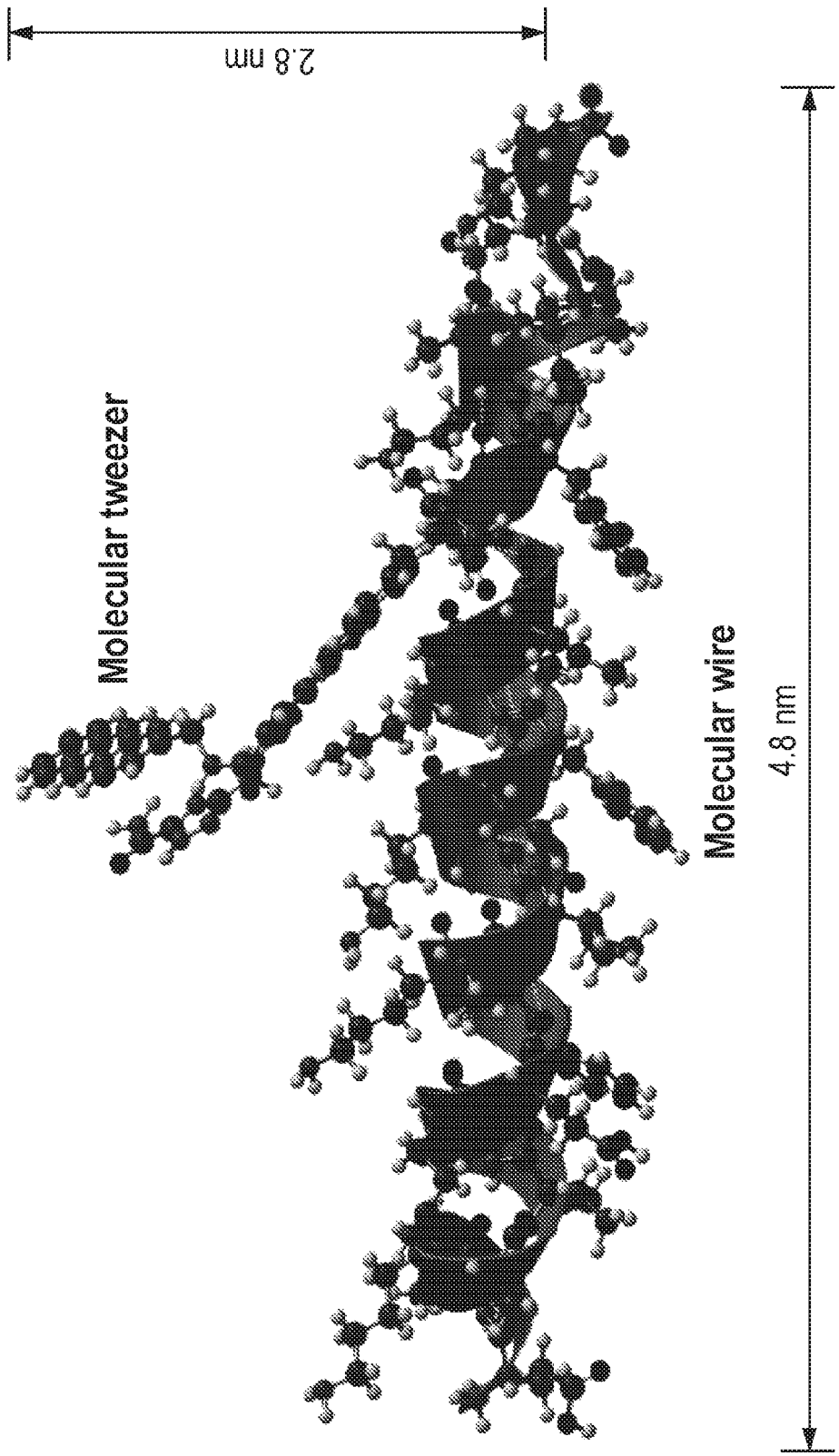
FIG. 10 shows a three-dimensional structure of a molecular tweezer-peptide conjugate (a) and its complex with a nucleobase in DNA (b).
FIG. 10(c) shows a route to synthesizing a molecular tweezer bearing two ethynyl groups (MT-2).
Figure 10B:
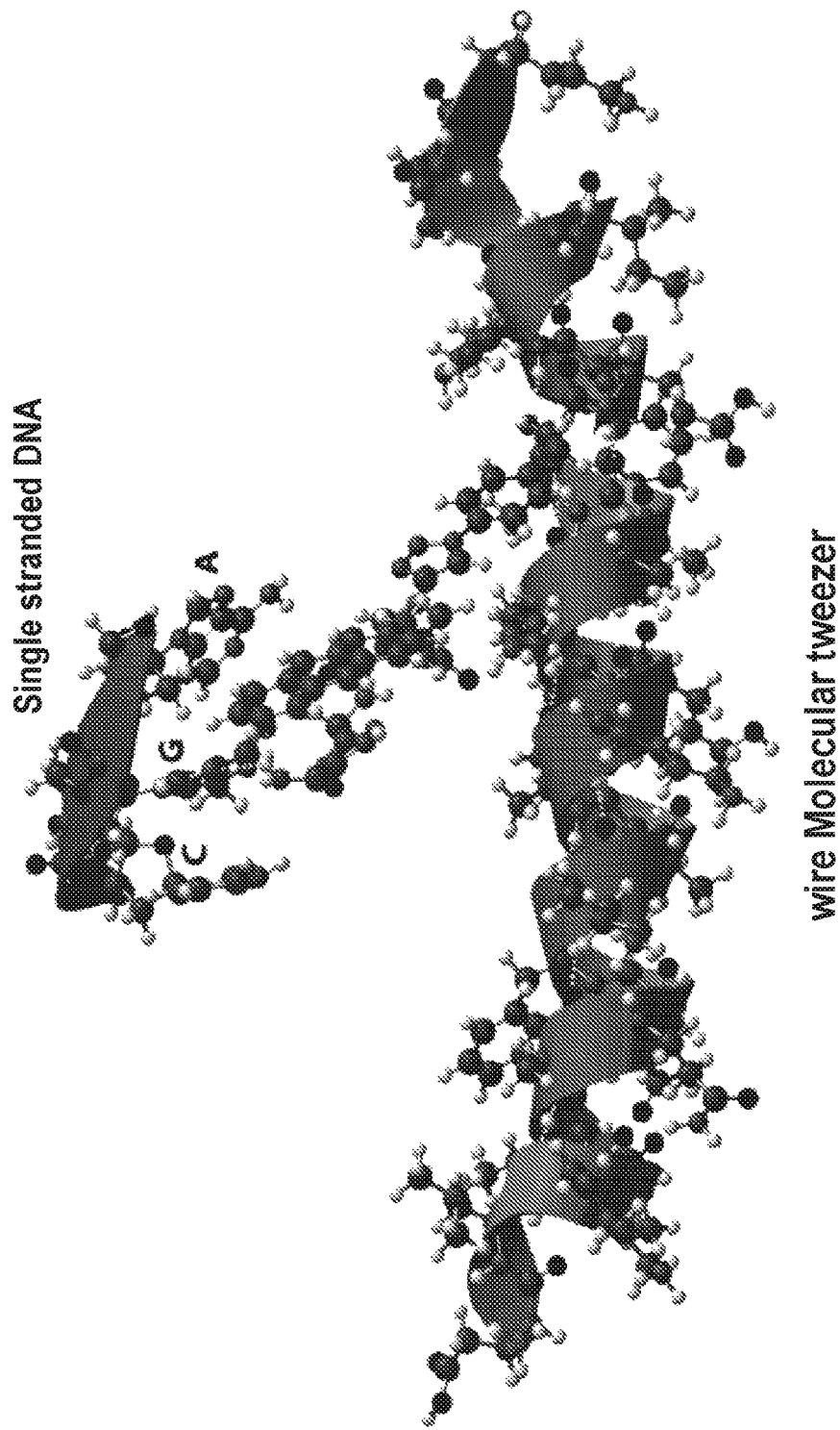
Figure 10C:
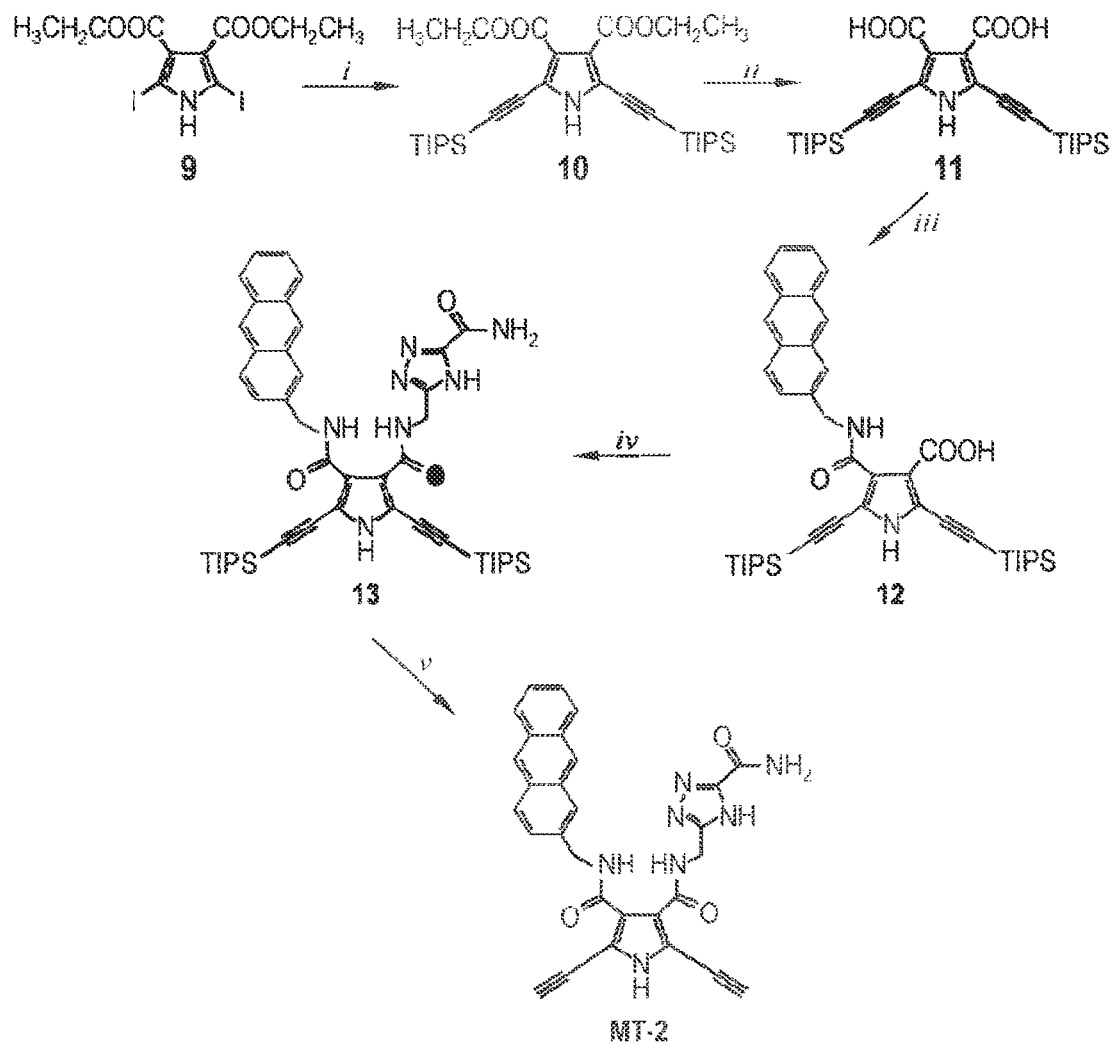

The molecular tweezer forms a conjugate with the said peptide wire through a click reaction (FIG. 10a). The conjugate interacts with individual nucleobase in a single-stranded DNA through the molecular tweezer (FIG. 10b).

In another embodiment, the invention provides a method to synthesize a molecular tweezer bearing two ethynyl functions (Scheme 3, MT-2) so that it can be incorporated into a peptide wire through forming a triazole isostere of the amide bond.

Figure 11:
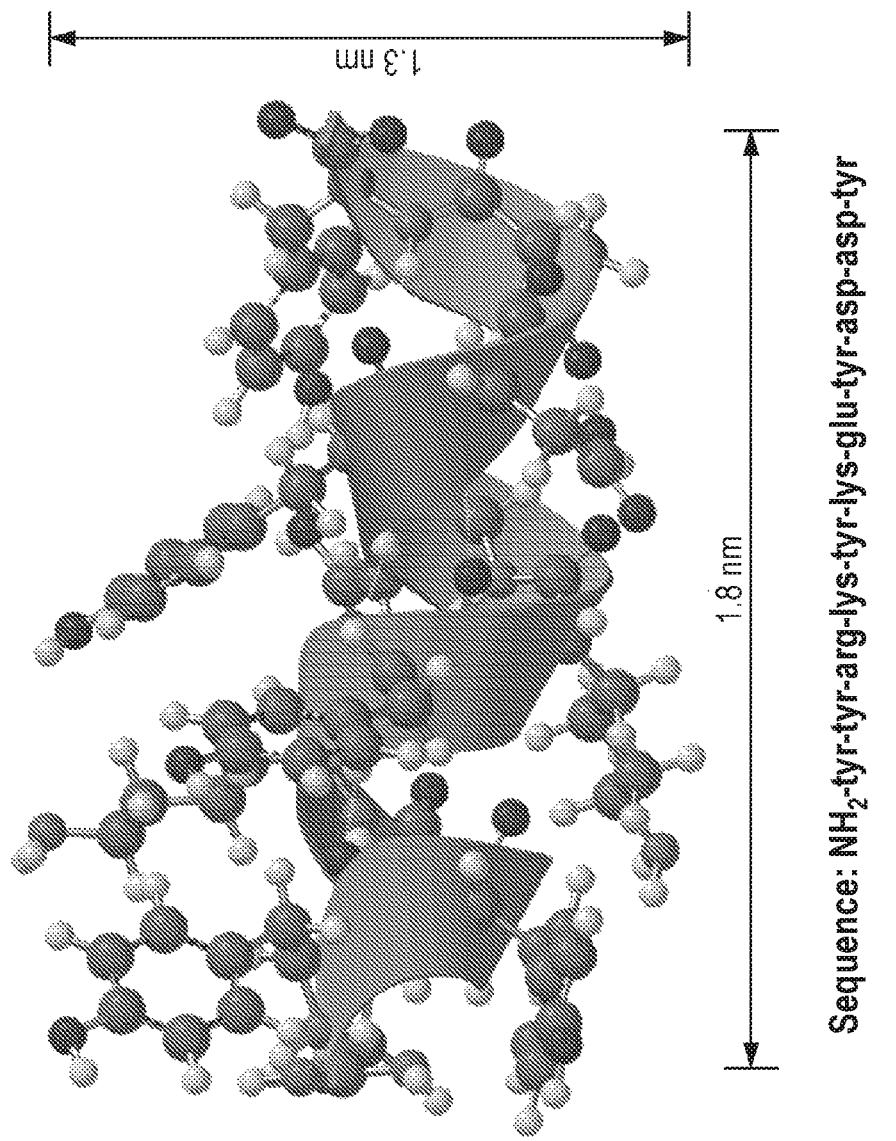
FIG. 11 shows the α helical structure of a short peptide wire with a high percentage of aromatic amino acid residues.

In some embodiments of the invention, the peptide wire is a short sequence with a higher percentage of aromatic amino acid residues: tyr-tyr-arg-lys-tyr-lys-glu-tyr-asp-asp-tyr (FIG. 11).[36]

Figure 12:
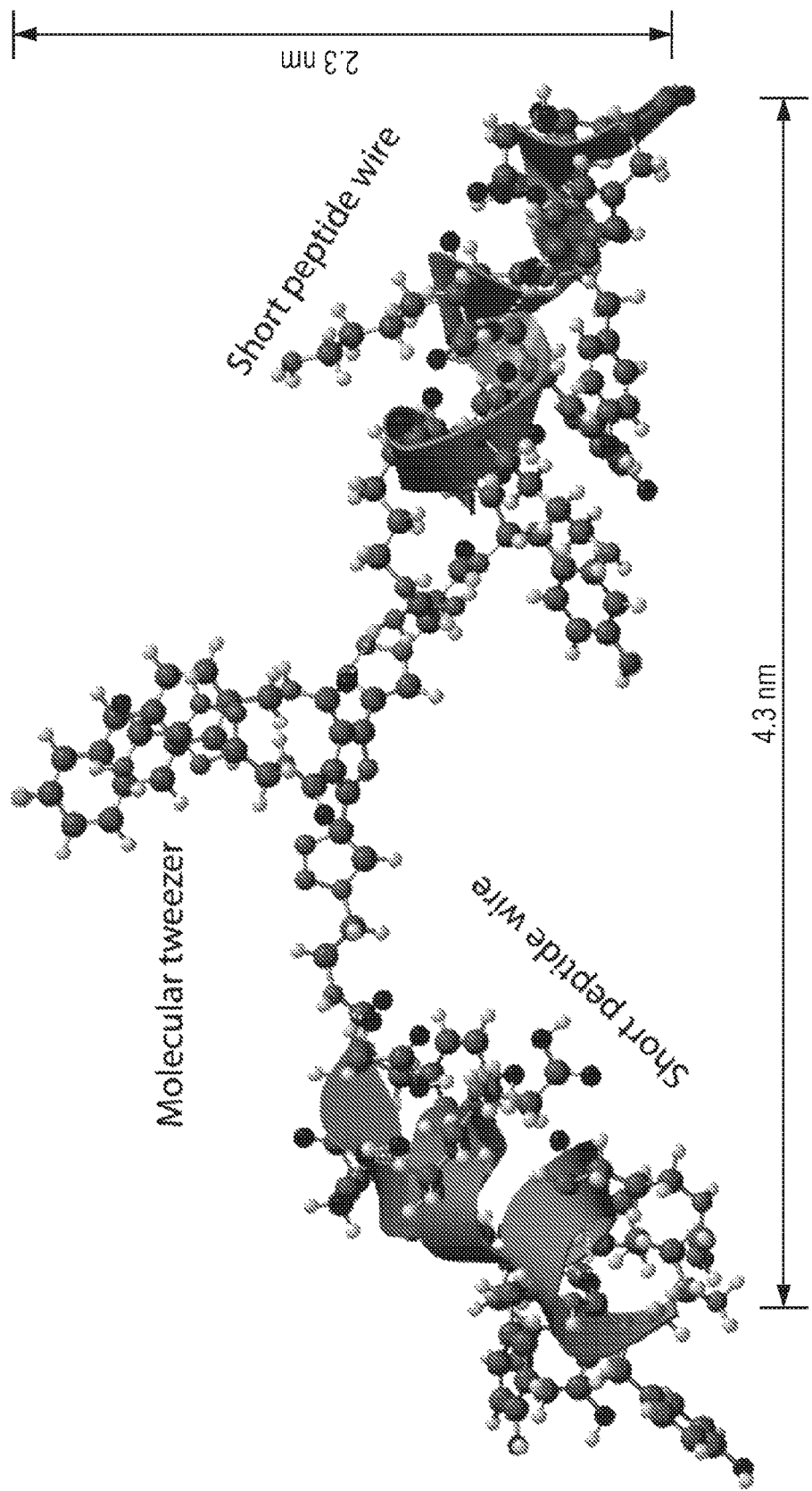
FIG. 12 shows the structure of a molecular tweezer-peptide wire hybrid.

Two short peptides are conjugated to the molecular tweezer through the triazole moieties to form a hybrid of two peptides and a molecular tweezer, which displays as a Y-shaped molecule (FIG. 12), wherein the molecular tweezer functions as a molecular switch. When interacting with nucleobases, it changes the current flow through the peptide wire by modulating its conformation.

Figure 13A:
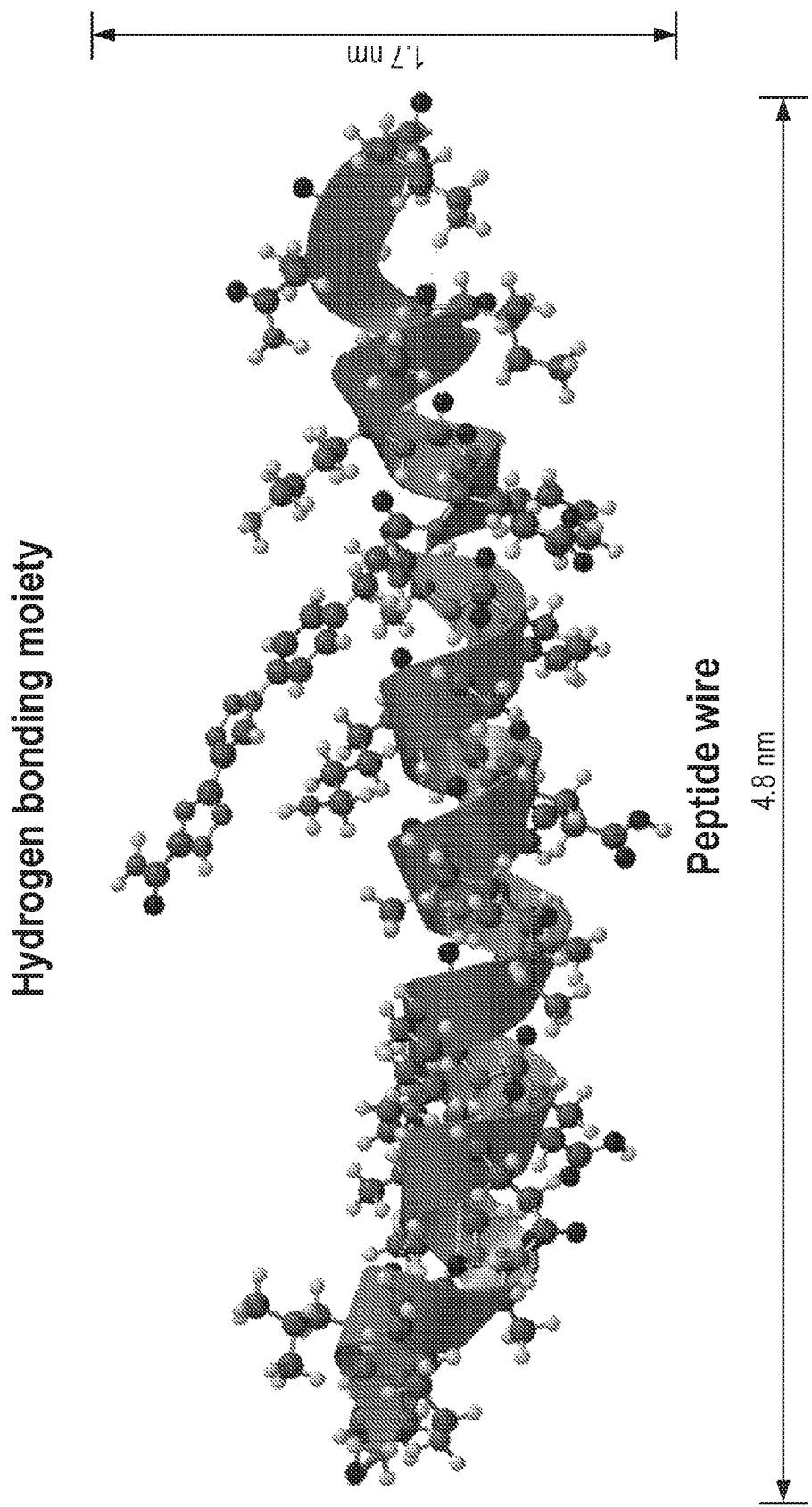
FIG. 13 shows structures of a conjugate of a peptide wire with a hydrogen bonding moiety (a) and a hybrid of the hydrogen bonding moiety incorporated into peptides (b).
Figure 13B:
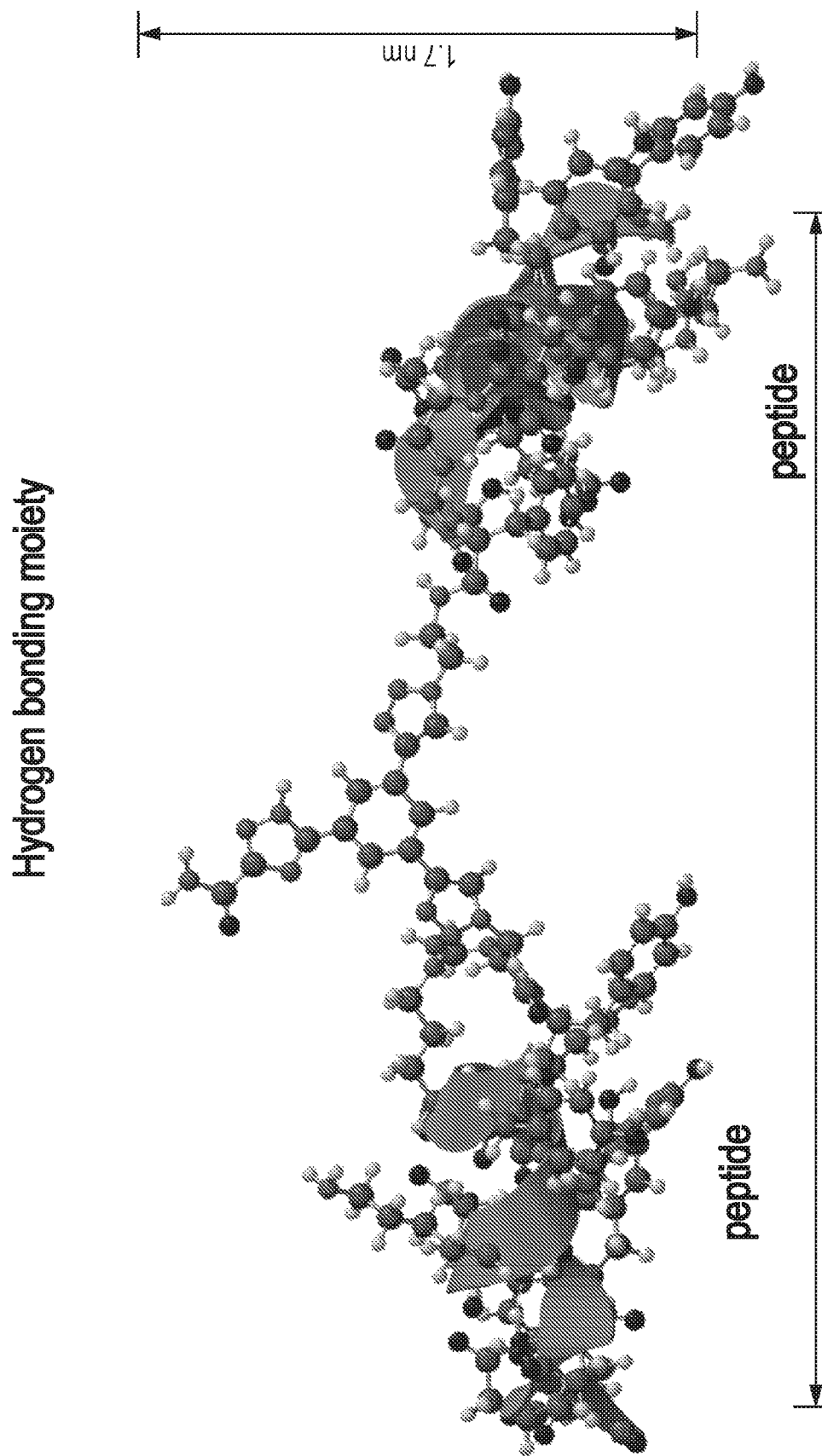

In one embodiment of the invention, it provides a conjugate of a peptide wire with a hydrogen-bonding moiety that interacts with nucleobases through hydrogen bonding (FIG. 13a) and a hybrid of the hydrogen bonding moiety with peptides (FIG. 13b). Compared with molecular tweezers, the hydrogen bonding moiety has weaker interactions with DNA nucleobases Some embodiments of the invention provide methods and reagents for connecting peptide wires, their conjugates, and their hybrids to electrodes. In one embodiment, the invention provides reagents cysteine (20) or (S)-2-amino-3-(1,2-dithiolan-4-yl)propanoic acid (21) that is synthesized following a method reported in literature[37] for functionalization of peptide wires at their N- and C-termini (FIG. 14). These reagents are incorporated into peptide wires by conventional peptide synthesis.

In some embodiments, the invention provides a tripod anchor for attaching peptide wires, their conjugates, and their hybrids to metal electrodes. Since the Au—S bond is only semi-covalent, a monothiol anchored monolayer is unstable enough, being readily displaced from the surface by other thiols. It can be desorbed from the surface within a few days when stored in phosphate buffer and exposed to elevated temperature and high salt concentrations. A tri-thio anchor would overcome those limits of the mono-thio anchor.[38]

Figure 15:
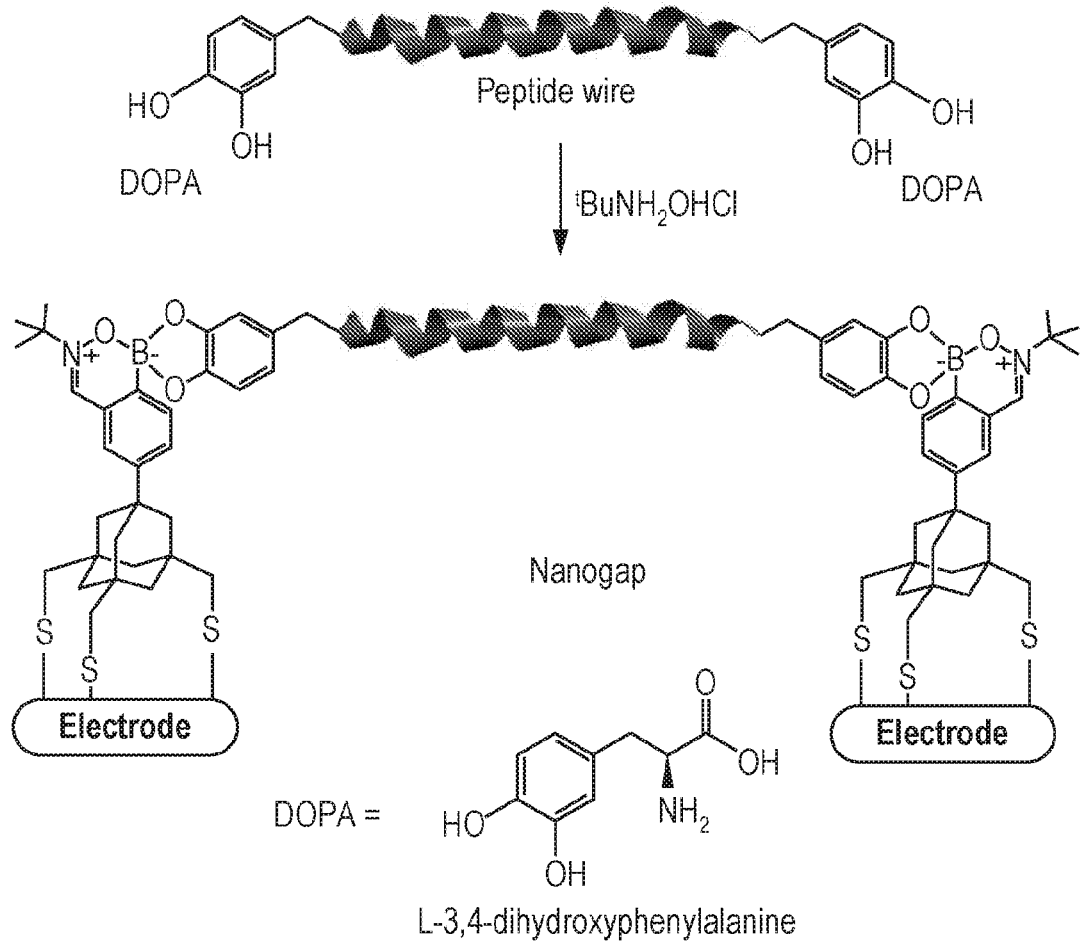
FIG. 15 shows a chemical process of attaching a peptide wire to metal electrodes functionalized with the tripod molecules.

In one embodiment, the invention provides a method to synthesize a tripod anchor (Scheme 4), the tripod carries a formylphenyl boronic acid function for anchoring of peptide wires. Its adamantane group makes the anchor more rigid than alkyl chain. The tripod provides a firm contact with metal surfaces, making the measurement reliable for the conductance of a single-molecule junction.[39] For the attachment of peptide wires, they are functionalized with 3,4-dihydroxyphenylalanine (DOPA) at their termini. In the presence of N-tert-butylhydroxylamine hydrochloride. DOPA specifically reacts with boronic acid to form a stable molecular junction (FIG. 15).[40]

Figure 16:
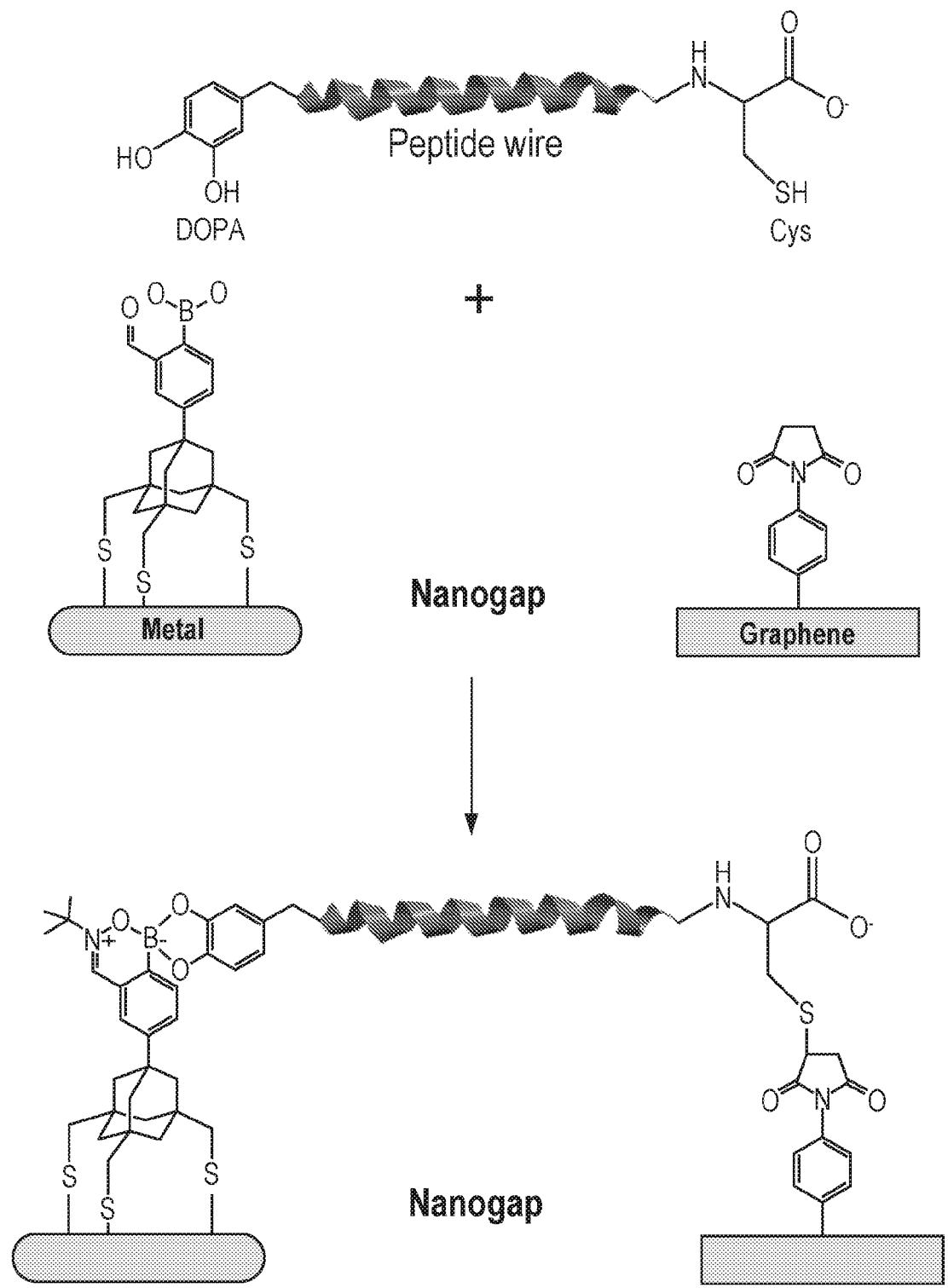
FIG. 16 shows a process of attaching a peptide wire to two electrodes composed of different materials that constitute a nanogap.

In one embodiment, the invention provides a method to attach peptide wires to electrodes composed of different materials that constituents a nanogap. FIG. 16 demonstrates an example of a nanogap comprising a metal electrode and a graphene electrode. For the attachment, the metal electrode is functionalized with the tripod anchor and the graphene with a p-(N-maleimido)phenyl function. Meanwhile, the peptide wire is modified with DOPA at its one terminal and with cysteine at the other end.[41] Thus, the peptide wire is attached to the two electrodes by two different reactions.

DETAILS

Computer modeling is performed in software Spartan '18 (Wavefunction, Inc). The 2D molecular structures are built-in ChemDraw pro v17, and then converted into 3D structures in Spartan '18. Each monomer structure is first subjected to energy minimization using the built-in Merck Molecular Force Field (MMFF) and then calculated using B3LYP/6-31G* in a water environment. The complexes are built with the aid of MMFF and calculated B3LYP/6-31G* in a water environment in Spartan '18. The bond energy of a complex is calculated by subtracting energies of individual monomers from the total energy of the complex.

Scheme 1 shows a method of synthesizing a molecular cleft with an ethynyl group (MC-1). The synthesis starts from 4-(trimethylsilyl)ethynylpyridine-2,6-dicarboxylate acid (1)[42] reacting with 2-natphthalenemethanamine (2) in the presence of DCC, giving a product 3 containing a trimethylsilyl protected ethynyl function. The protecting group can be removed by treating compound 3 with $^n$Bu$_4$NF, furnishing the final product MC-1 that can be attached to molecular wires.

Scheme 2 shows a method of synthesizing another molecular cleft with an ethynyl group (MT-1). The synthesis starts from dimethyl 1H-pyrrole-3,4-dicarboxylate (4) reacting with bromoethynyltriisopropylsilane, which is catalyzed by a copper complex,[43] giving a product (5) containing a triisopropylsilyl (TIPS)-protected ethynyl function. Compound 5 is converted to a dicarboxylic acid (6) by hydrolysis under a basic condition. Subsequently, compound 6 reacts with 2-(aminomethyl)anthracene and 5-(aminomethyl)-1,2,4-triazole-3-carboxamide in the presence of DCC, giving a molecular cleft product with a triisopropyisilyl (TIPS)-protected ethynyl function (8). The desired product (MC-2) is obtained by removing the TIPS protecting group with tetra-n-butylammonium fluoride (TBAF).

Scheme 4 shows a method to synthesize an anchor molecule with a trivalent sulfhydryl function (A-1). The starting material 1-(4-Bromophenyl)-3,5,7-tris(trifluoromethanesulfonylmethyl)adamantane (14) is synthesized following the method reported in the literature.[44] First, it is formylated by reacting with dichloromethyl methyl ether (Cl$_2$CHOMe) in the presence of silver trifluoromethanesulfonate (AgOTf), furnishing aldehyde 15, which is sequentially converted to acetal 16.[45] Then, compound 16 is treated with potassium thioacetate, resulting in a thiolated compound (17). Compound 17 is converted to boronic acid 18 by photoinduced borylation.[46] The desired compound 19 is obtained by deacetylation with acid. The acetyl group will be removed in situ using pyrrolidine during the process of functionalizing the electrodes.

More specifically, this invention includes the following:
1) A device for direct electrical identification and/or sequencing of biopolymers comprising:
   a. a silicon chip, placed between a cis chamber and a trans chamber where a nanopore is embedded with an effective thickness that can accommodate at least a portion of the polymer molecule when it is translocated from the cis chamber to the trans chamber;
   b. a first electrode and a second electrode, embedded in the nanopore and overlapping each other, separated by a dielectric layer to form a nanogap between them;
   c. a synthetic T- or Y-shaped modular module that can function as a bridge between the two electrodes, allowing an electric current to flow from one end to another; and a receptor that can capture the biopolymer through interacting with its constituents. The interaction causes conformation changes of the receptor as well as in the remaining portion of the molecule so that the electric current flowing through one electrode to another is altered, hence, the biopolymer or its monomers can be identified;
where the silicon chip can have a single nanopore or plurality of nanopores; the electrodes can have the same material or different materials, for example, a metal such as gold, silver, palladium, platinum, or metal alloys, and a conductive non-metal, such as graphene, or two different metals or two different conductive non-metals. Different materials allow the molecular bridge to connect to the electrodes in a controlled way. The dielectric layer between the two electrodes has a thickness between 3 to 40 nm, preferably 4 to 10 nm. The bridging molecule can be synthesized as one molecule, or constructed by conjugating molecular tweezers (cleft receptor structure) with a molecular wire (a linear structure).

2) A device for direct electrical identification and/or sequencing of a biopolymer comprising:
   the same components as the device described above except the pair of electrodes is fabricated in the same plane on the surface of nanopore, either at the entrance side or on the exit side, separated by a nanogap with a distance between 2 to 100 nm, preferably 3 to 10 nm; wherein the nanogap is located at the center of the nanopore, off the center, or along the nanopore edge.

3) A device for direct electrical identification and/or sequencing of biopolymers comprising:
   a. A nanochannel with progressively reducing channel size, wherein the nanochannel reduces its size either continuously and smoothly, or stepwise, and either with or without microstructures on the floor or wall that help stretching and slow down the biopolymer;

b. A first electrode and a second electrode, placed at the end of the nanochannel with the first electrode embedded at one side of the nanochannel and the second electrode embedded at the other side of the nanochannel, opposite to each other, forming a nanogap between them; Alternatively, both electrodes embedded at the same side of the nanochannel with a dielectric layer between them, similar to the arrangement in the nanopore device described in 1) but always lying at the end of the nanochannel; Similar to device 1), the electrodes are made of the same or different materials.

c. A synthetic T- or Y-shaped modular module that can function as a bridge between the two electrodes, allowing an electric current to flow from one end to another; and a receptor that can capture the biopolymer through interacting with its constituents. The interaction causes conformation changes of the receptor as well as in the remaining portion of the molecule so that the electric current flowing through one electrode to another is altered, hence, the biopolymer or its monomers cause electrical signatures for their identification;

4) A system for direct electrical identification and/or sequencing of a biopolymer comprising:
   a. One of the devices described in 1) to 3);
   b. A mechanism for controlling the movement of biopolymers through the nanopore or nanochannel in sub-nanometer precision;
   c. A bias source for applying bias voltage between the cis chamber and the trans chamber to direct one end of the biopolymer to enter the nanopore;
   d. A voltage source for applying a voltage between the two electrodes for the measurement of electrical current fluctuations through the bridging molecule;
   e. Software for signal acquisition and analysis.

Where the biopolymer can be DNA, RNA, protein, peptide, polysaccharides, etc.; the movement control mechanism can be a piezo drive, an electromechanical drive, a magnetic or electrical means or a combination of any of them, such as those control mechanism described in PCT WO2017075620A1, that is able to achieve a sub-nanometer precision; the system above may have a scan plate to which the biopolymer can attach either through chemical bonding or through a magnetic bead, and the scan plate is moved by a nanometer precision actuator. The controlled movement speed is between 0.1 ms to 1000 ms per monomer or base, preferably 1 ms to 100 ms, and most preferably 5 ms to 20 ms.

5) A method for the identification and/or sequencing of biopolymers
   a. Providing a device from one of the devices described in 1) to 2);
   b. Functionalizing electrodes to facilitate the attachment of the molecular module; using different electrode materials and attachment chemistry to attach the molecular module in a controlled way;
   c. Attaching the first end of the biopolymer to a magnetic bead either directly or through a linker molecule, using the methods described in the PCT patent WO2017075620A1;
   d. Aligning the biopolymer with a nanopore equipped with the bridging molecule with a molecular probe using one of the methods described in the PCT patent WO20175620A1;
   e. Directing a second end of the biopolymer to the nanopore by an electrophoretic force;
   f. Moving the biopolymer through the nanopore in a precisely controlled way described in the PCT patent WO20175620A1,
   g. Applying voltage bias to the two electrodes and measuring the electric current fluctuations causing by the interaction between the molecular module and the biopolymer.

6) A method for the identification and/or sequencing of biopolymers of:
   a. Providing a device described in 3);
   b. Functionalizing the electrodes to facilitate the attachment of the molecular module; using different electrode materials and attachment chemistry to attach the molecular module in a controlled way;
   c. Attaching the first end of the biopolymer to a bead or nanoparticle either directly or through a molecular linker;
   d. Moving the biopolymer through the nanochannel by fluid flow or by an electrophoretical force;
   e. Applying voltage bias to the two electrodes and measuring the electric current fluctuations when the biopolymer passes through the nanogap.

The said molecular module is composed of a conductive moiety and a capture (cleft or tweezer) moiety;

Where the said capture portion is
a) A planar structure that can interact with biopolymer through hydrogen bonding or aromatic stacking
b) A moiety that is composed of two planar structures linked together by a spacing molecule, which can interact with a chemical entity through hydrogen bonding, aromatic stacking, or both hydrogen bonding and aromatic stacking.
c) A structure that interacts with DNA or RNA nucleobases through hydrogen bonding or base stacking.
d) Molecular clefts that trap DNA or RNA nucleobases in its cavity.
e) Molecular tweezers or clips that capture DNA or RNA nucleobases through hydrogen bonding and base stacking.
f) Those that can distinguish among nucleobases by forming different noncovalent complexes that have different binding energies.

Where the said conductive moiety comprises
a) An organic molecule whose conformation can be changed and subsequently its conductivity. Specifically, those molecules contain aromatic structures.
b) A natural nucleic acid that has a double helix structure and contains G-C base pairs.
c) A natural nucleic acid that has a double helix structure and contains modified base(s), modified nucleoside(s), or modified nucleotide(s)
d) A DNA analogy that forms a double helix structure and composes natural nucleobases.
e) A DNA analogy that forms a double helix structure and contains unnatural nucleobases.
f) A DNA analogy that comprises unnatural bases and forms a double helix structure.
g) A DNA analogy that is composed of a non-phosphate backbone
h) A peptide that has an $\alpha$ helix or a $\beta$ sheet structure and contains aromatic amino acids and charged amino acids.
i) A peptide that contains unnatural aromatic amino acids.
j) A peptide that is composed of a non-amide backbone The said molecular wire (or wires) in the devices described above has a length of 2 nm to 1 µm, containing anchoring molecules at their ends that can react with electrodes to form covalent bonds.

The said electrodes in the devices described in 1), 2) and 3) are
- a) Metal electrodes that can directly react with the said anchoring molecules.
- b) Metal electrodes that can be functionalized on their surfaces by self-assembling monolayers that can react with anchoring molecules to form covalent bonds.
- c) Metal oxide electrodes that can be functionalized with silanes that can react with anchoring molecules to form covalent bonds.
- d) Carbon electrodes that can be functionalized with organic reagents that can react with anchoring molecules to form covalent bonds.

The said anchoring molecules here are
- a) Those that contain an amino group or groups.
- b) Those that contain a thiol group or groups.
- c) Those that contain a disulfide group or groups.
- d) Those that contain a diol group or groups.

The said monolayer here is formed by
- a) Same organic molecules each of which that bears a thiol group with a length of 0.2 to 3 nm.
- b) Same organic molecules each of which bears multiple thiol groups with a length of 0.2 to 3 nm.
- c) Same organic molecules said in 9-a and 9-b that contain a functional group that can react with anchoring group in claim 8
- d) A thiol tripod that forms monolayers on the said metal surface and reacts with the said anchoring molecules.
- e) A mixture of the said organic reagents or a mixture of the said organic molecules and the thiol tripod.

GENERAL REMARKS

All publications, patents, and other documents mentioned herein are incorporated by reference in their entirety. Unless defined otherwise, all technical and scientific terms used herein have the same meaning as those commonly understood by one of ordinary skill in the art to which this invention belongs. While the present invention has been illustrated by a description of various embodiments and while these embodiments have been described in considerable detail, it is not the intention of the applicants to restrict or in any way limit the scope of the applications. Additional advantages and modifications will readily appear to those skilled in the art. The invention in its broader aspects is therefore not limited to the specific details, representative device, apparatus and method, and illustrative example shown and described. Accordingly, departures may be made from such details without departing from the spirit of the applicant's general inventive concept.

REFERENCES

1. Armentano, D.; De Munno, G.; Di Donna, L.; Sindona, G.; Giorgi, G.; Salvini, L.; Napoli, A., Self-assembling of cytosine nucleoside into triply-bound dimers in acid media. A comprehensive evaluation of proton-bound pyrimidine nucleosides by electrospray tandem mass spectrometry, X-rays diffractometry, and theoretical calculations. *Journal of the American Society for Mass Spectrometry* 2004, 15, 268-79.
2. Goodwin, S.; McPherson, J. D.; McCombie, W. R., Coming of age: ten years of next-generation sequencing technologies. *Nature reviews. Genetics* 2016, 17, 333-51.
3. Metzker, M. L., Emerging technologies in DNA sequencing. *Genome Res* 2005, 15, 1767-76.
4. Treangen, T. J.; Salzberg, S. L., Repetitive DNA and next-generation sequencing: computational challenges and solutions. *Nature reviews. Genetics* 2012, 13, 36-46.
5. Rhoads, A.; Au, K. F., PacBio Sequencing and Its Applications. *Genomics Proteomics Bioinformatics* 2015, 13, 278-89.
6. Gordon, D.; Huddleston, J.; Chaisson, M. J. P.; Hill, C. M.; Kronenberg, Z. N.; Munson, K. M.; Malig, M.; Raja, A.; Fiddes, I.; Hillier, L. W.; Dunn, C.; Baker, C.; Armstrong, J.; Diekhans, M.; Paten, B.; Shendure, J.; Wilson, R. K.; Haussler, D.; Chin, C.-S.; Eichler, E. E., Long-read sequence assembly of the gorilla genome. *Science* 2016, 352, aae0344-1.
7. Mukhopadhyay, R., DNA sequencers: the next generation. *Analytical Chemistry* 2009, 8, 1736-1740.
8. Deamer, D.; Akeson, M.; Branton, D., Three decades of nanopore sequencing. *Nat Biotechnol* 2016, 34, 518-24.
9. Jain, M.; Fiddes, I. T.; Miga, K. H.; Olsen, H. E.; Paten, B.; Akeson, M., Improved data analysis for the MinION nanopore sequencer. *Nature methods* 2015, 12, 351-6.
10. Manrao, E. A.; Derrington, I. M.; Laszlo, A. H.; Langford, K. W.; Hopper, M. K.; Gillgren, N.; Pavlenok, M.; Niederweis, M.; Gundlach, J. H., Reading DNA at single-nucleotide resolution with a mutant MspA nanopore and phi29 DNA polymerase. *Nat Biotechnol* 2012, 30, 349-353.
11. Laszlo, A. H.; Derrington, I. M.; Ross, B. C.; Brinkerhoff, H.; Adey, A.; Nova, I. C.; Craig, J. M.; Langford, K. W.; Samson, J. M.; Daza, R.; Doering, K.; Shendure, J.; Gundlach, J. H., Decoding long nanopore sequencing reads of natural DNA. *Nature Biotechnology* 2014, 32, 829-833.
12. Lindsay, S., The promises and challenges of solid-state sequencing. *Nat Nanotechnol* 2016, 11, 109-11.
13. Lagerqvist, J.; Zwolak, M.; Ventra, M. D., Fast DNA Sequencing via Transverse Electronic Transport. *Nano Lett* 2006, 6, 779-782.
14. Di Ventra, M.; Taniguchi, M., Decoding DNA, RNA and peptides with quantum tunnelling. *Nat Nanotechnol* 2016, 11, 117-26.
15. Tsutsui, M.; Taniguchi, M.; Yokota, K.; Kawai, T., Identifying single nucleotides by tunnelling current. *Nat Nanotechnol* 2010, 5, 286-90.
16. Tsutsui, M.; Rahong, S.; Iizumi, Y.; Okazaki, T.; Taniguchi, M.; Kawai, T., Single-molecule sensing electrode embedded in-plane nanopore. *Scientific reports* 2011, 1, 46.
17. Alvarez, J. R.; Skachkov, D.; Massey, S. E.; Kalitsov, A.; Velev, J. P., DNA/RNA transverse current sequencing: intrinsic structural noise from neighboring bases. *Frontiers in genetics* 2015, 6, 213.
18. Prasongkit, J.; Feliciano, G. T.; Rocha, A. R.; He, Y.; Osotchan, T.; Ahuja, R.; Scheicher, R. H., Theoretical assessment of feasibility to sequence DNA through interlayer electronic tunneling transport at aligned nanopores in bilayer graphene. *Scientific reports* 2015, 5, 17560.
19. Biswas, S.; Sen, S.; Im, J.; Biswas, S.; Krstic, P.; Ashcroft, B.; Borges, C.; Zhao, Y.; Lindsay, S.; Zhang, P., Universal Readers Based on Hydrogen Bonding or pi-pi Stacking for Identification of DNA Nucleotides in Electron Tunnel Junctions. *ACS Nano* 2016, 10, 11304-11316.
20. Olsen, T. J.; Choi, Y.; Sims, P. C.; Gul, O. T.; Corso, B. L.; Dong, C.; Brown, W. A.; Collins, P. G.; Weiss, G. A., Electronic measurements of single-molecule processing by DNA polymerase I (Klenow fragment). *J Am Chem Soc* 2013, 135, 7855-60.

21. Pugliese, K. M.; Gul, O. T.; Choi, Y.; Olsen, T. J.; Sims, P. C.; Collins, P. G.; Weiss, G. A., Processive Incorporation of Deoxynucleoside Triphosphate Analogs by Single-Molecule DNA Polymerase I (Klenow Fragment) Nanocircuits. *J Am Chem Soc* 2015, 137, 9587-94.
22. Xie, P.; Xiong, Q.; Fang, Y.; Qing, Q.; Lieber, C. M., Local electrical potential detection of DNA by nanowire-nanopore sensors. *Nature Nanotechnology* 2012, 7, 119-125.
23. Nakatsuka, N.; Yang, K.-A.; Abendroth, J. M.; Cheung, K. M.; Xu, X.; Yang, H.; Zhao, C.; Zhu, B.; Rim, Y. S.; Yang, Y.; Weiss, P. S.; Stojanović, M. N.; Andrews, A. M., Aptamer-field-effect transistors overcome Debye length limitations for small-molecule sensing. *Science* 2018, 362, 319-324.
24. Wang, G.; Kim, T.-W.; Jang, Y. H.; Lee, T., Effects of Metal-Molecule Contact and Molecular Structure on Molecular Electronic Conduction in Nonresonant Tunneling Regime: Alkyl versus Conjugated Molecules. *J. Phys. Chem. C* 2008, 112, 13010-13016.
25. Xin, N.; Wang, J.; Jia, C.; Liu, Z.; Zhang, X.; Yu, C.; Li, M.; Wang, S.; Gong, Y.; Sun, H.; Zhang, G.; Liu, Z.; Zhang, G.; Liao, J.; Zhang, D.; Guo, X., Stereoelectronic Effect-Induced Conductance Switching in Aromatic Chain Single-Molecule Junctions. *Nano Lett.* 2017, 17, 856-861.
26. Fujii, S.; Tada, T.; Komoto, Y.; Osuga, T.; Murase, T.; Fujita, M.; Kiguchi, M., Rectifying Electron-Transport Properties through Stacks of Aromatic Molecules Inserted into a Self-Assembled Cage. *J Am Chem Soc* 2015, 137, 5939-47.
27. Chen, Y.-S.; Hong, M.-Y.; Huang, G. S., A protein transistor made of an antibody molecule and two gold nanoparticles. *Nature Nanotechnology* 2012, 7, 197-203.
28. Amdursky, N., Electron Transfer across Helical Peptides. *ChemPlusChem* 2015, 80, 1075-1095.
29. Reguera, G.; McCarthy, K. D.; Mehta, T.; Nicoll, J. S.; Tuominen, M. T.; Lovley, D. R., Extracellular electron transfer via microbial nanowires. *Nature* 2005, 435, 1098-101.
30. Petrov, E. G.; Shevchenko, Y. V.; Teslenko, V. I.; May, V., Nonadiabatic donor-acceptor electron transfer mediated by a molecular bridge: A unified theoretical description of the superexchange and hopping mechanism. *The Journal of chemical physics* 2001, 115, 7107-7122.
31. Malak, R. A.; Gao, Z.; Wishart, J. F.; Isied, S. S., Long-Range Electron Transfer Across Peptide Bridges: The Transition from Electron Superexchange to Hopping. *J. AM. CHEM. SOC.* 2004, 126, 13888-13889.
32. Qing, Q.; Wang, Y.; Sadar, J. NANOPORE DEVICES FOR SENSING BIOMOLECULES. 2018, US 2018/0280968.
33. Sadara, J.; Wang, Y.; Qing, Q., Confined Electrochemical Deposition in Sub-15 nm Space for Preparing Nanogap Electrodes. *ECS Transactions* 2017, 77, 65-72
34. Ing, N. L.; Spencer, R. K.; Luong, S. H.; Nguyen, H. D.; Hochbaum, A. I., Electronic Conductivity in Biomimetic alpha-Helical Peptide Nanofibers and Gels. *ACS Nano* 2018, 12, 2652-2661.
35. Raliski, B. K.; Howard, C. A.; Young, D. D., Site-Specific Protein Immobilization Using Unnatural Amino Acids. *Bioconjug Chem* 2014, 25, 1916-1920.
36. Kalyoncu, E.; Ahan, R. E.; Olmez, T. T.; Safak Seker, U. O., Genetically encoded conductive protein nanofibers secreted by engineered cells. *RSC Advances* 2017, 7, 32543-32551.
37. Morera, E.; Pinnen, F.; Lucente, G., Synthesis of 1,2-Dithiolane Analogues of Leucine for Potential Use in Peptide Chemistry. *Organic Letters* 2002, 4, 1139-1142.
38. Staderini, M.; Gonzalez-Fernandez, E.; Murray, A. F.; Mount, A. R.; Bradley, M., A tripod anchor offers improved robustness of peptide-based electrochemical biosensors. *Sensors and Actuators B: Chemical* 2018, 274, 662-667.
39. Lee, S. U.; Mizuseki, H.; Kawazoe, Y., Rigid adamantane tripod linkage for well-defined conductance of a single-molecule junction. *Physical chemistry chemical physics: PCCP* 2010, 12, 11763-9.
40. Meadows, M. K.; Roesner, E. K.; Lynch, V. M.; James, T. D.; Anslyn, E. V., Boronic Acid Mediated Coupling of Catechols and N-Hydroxylamines: A Bioorthogonal Reaction to Label Peptides. *Org Lett* 2017, 19, 3179-3182.
41. Neubert, T. J.; Rösicke, F.; Sun, G.; Janietz, S.; Gluba, M. A.; Hinrichs, K.; Nickel, N. H.; Rappich, J., Functionalization of gold and graphene electrodes by p-maleimido-phenyl towards thiol-sensing systems investigated by EQCM and IR ellipsometric spectroscopy. *Applied Surface Science* 2017, 421, 755-760.
42. Tong, L.; Gothelid, M.; Sun, L., Oxygen evolution at functionalized carbon surfaces: a strategy for immobilization of molecular water oxidation catalysts. *Chem Commun* 2012, 48, 10025-7.
43. Kerwin, S.; Reinus, B., A Copper-Catalyzed N-Alkynylation Route to 2-Substituted N-Alkynyl Pyrroles and Their Cyclization into Pyrrolo[2,1-c]oxazin-1-ones: A Formal Total Synthesis of Peramine. *Synthesis* 2017, 49, 2544-2554.
44. Kitagawa, T.; Idomoto, Y.; Matsubara, H.; Hobara, D.; Kakiuchi, T.; Okazaki, T.; Komatsu, K., Rigid Molecular Tripod with an Adamantane Framework and Thiol Legs. Synthesis and Observation of an Ordered Monolayer on Au(111). *J. Org. Chem.* 2006, 71, 1362-1369.
45. Ohsawa, K.; Yoshida, M.; Doi, T., A direct and mild formylation method for substituted benzenes utilizing dichloromethyl methyl ether-silver trifluoromethanesulfonate. *J Org Chem* 2013, 78, 3438-44.
46. Mfuh, A. M.; Doyle, J. D.; Chhetri, B.; Arman, H. D.; Larionov, O. V., Scalable, Metal- and Additive-Free, Photoinduced Borylation of Haloarenes and Quaternary Arylammonium Salts. *J Am Chem Soc* 2016, 138, 2985-2988.

What is claimed:

1. A system for electrical identification and/or sequencing of a biopolymer comprising:
   a. a substrate placed between a cis reservoir and a trans reservoir;
   b. a nanopore in the substrate allowing at least a portion of the biopolymer to translocate from the cis reservoir to the trans reservoir;
   c. a first electrode and a second electrode, embedded in the nanopore and overlapping each other, separated by a dielectric layer to form a nanogap between them;
   d. a synthetic T- or Y-shaped molecular module with a conductive molecular wire having anchoring molecules at its ends for attachment that can bridge the two electrodes, allowing an electric current to flow from one electrode to the other, and a receptor that can interact with the biopolymer or its constituent monomers for sensing;
   e. a mechanism configured to control the speed of the biopolymer moving through the nanopore;
   f. a first bias source for applying a bias voltage between the cis reservoir and the trans reservoir that facilitates the biopolymer moving through the nanopore;
   g. a second bias source for applying a bias voltage between the two electrodes; and
   h. a measuring system configured to measure and analyze a signal as the biopolymer passes through the nanopore affecting the electric current and based on the signal to identify the biopolymer or its constituent monomers.

2. A system for electrical identification and/or sequencing of a biopolymer comprising:
   a. a substrate placed between a cis reservoir and a trans reservoir;
   b. a nanopore in the substrate allowing at least a portion of the biopolymer to translocate from the cis reservoir to the trans reservoir;
   c. a pair of electrodes separated by a nanogap in the same plane on the surface of the nanopore, either at the entrance side or on the exit side, wherein the nanogap is located at the center of the nanopore, off the center, or along the nanopore edge;
   d. a synthetic T- or Y-shaped molecular module with a conductive molecular wire having anchoring molecules at its ends for attachment that can bridge the two electrodes, allowing an electric current to flow from one electrode to the other, and a receptor that can interact with the biopolymer or its constituent monomers for sensing;
   e. a mechanism configured to control the speed of the biopolymer moving through the nanopore;
   f. a first bias source for applying a bias voltage between the cis reservoir and the trans reservoir that facilitates the biopolymer moving through the nanopore;
   g. a second bias source for applying a bias voltage between the two electrodes; and
   h. a measuring system configured to measure and analyze a signal as the biopolymer passes through the nanopore affecting the electric current and based on the signal to identify the biopolymer or its constituent monomers.

3. A system for electrical identification and/or sequencing of a biopolymer comprising:
   a. a planar substrate with a cis reservoir and a trans reservoir;
   b. a nanochannel in the substrate that allows at least a portion of the biopolymer to move from the cis reservoir to the trans reservoir through the nanochannel, wherein the nanochannel reduces its size progressively either continuously or stepwise, and either with or without microstructures on the floor or wall of the nanochannel thus configured to stretch and slow the progression of the biopolymer;
   c. a first electrode and a second electrode positioned opposite to each other at the end of the nanochannel with the first electrode embedded on the wall on one side of the nanochannel and the second electrode embedded on the wall on the other side of the nanochannel, forming a nanogap between them with gap size equal to the local width of the nanochannel; or alternatively, both electrodes embedded on the wall on the same side of the nanochannel with a dielectric layer between them, forming a nanogap between them with the gap size equal to the thickness of the dielectric layer;
   d. a synthetic T- or Y-shaped molecular module with a conductive molecular wire having anchoring molecules at its ends for attachment that can bridge the two electrodes, allowing an electric current to flow from one electrode to the other, and a receptor that can interact with the biopolymer or its constituent monomers for sensing;

e. a mechanism configured to control the speed of the biopolymer moving through the nanochannel;
f. a first bias source for applying a bias voltage between the cis reservoir and the trans reservoir that facilitates the biopolymer moving through the nanochannel;
g. a second bias source for applying a bias voltage between the two electrodes; and
h. a measuring system configured to measure and analyze a signal as the biopolymer passes through the nanochannel affecting the electric current and based on the signal to identify the biopolymer or its constituent monomers.

4. The system of claim 1, wherein
the biopolymer is DNA, RNA, protein, oligos, peptides, polysaccharides, or a combination of them, either natural, modified or synthesized.

5. The system of claim 1, wherein
the substrate is a nanochip comprising a plurality of nanopores or nanochannels.

6. The system of claim 1, wherein
the mechanism configured to control the speed of the biopolymer moving through the nanopore comprises the following:
a. a scan plate placed substantially parallel to the substrate, to which the biopolymer is directly or indirectly attached; and
b. an actuator that is used to control the relative movement between the substrate and the scan plate with nanometer precision; wherein the relative movement is either in the normal direction (change the distance between the scan plate and the substrate) or in the tangential direction (lateral movement, without changing the distance between the scan plate and the substrate).

7. The system of claim 6, wherein
the actuator is a precision linear motion stage driven by a piezoelectric effect drive, an electromechanical drive, or any drive using a magnetic component, an electrical component, or a mechanical or a combination of them.

8. The system of claim 6, wherein
the biopolymer attaches to the scan plate either directly through a chemical bond, a covalent or non-covalent bond, or indirectly through a magnetic bead or a linker molecule, or a combination thereof.

9. The system of claim 8, wherein
the linker molecule is selected from the group consisting of a single-stranded nucleic acid, a double-stranded nucleic acid, a polypeptide chain, a cellulose fiber or any flexible linear polymer, either natural, modified or synthesized, and a combination thereof.

10. The system of claim 1, wherein
the mechanism configured to control the speed of the biopolymer moving through the nanopore comprises an enzyme, an enzyme with a conditioned media that can slow down enzyme activity, a viscous media, a porous media or any media that can slow down the biopolymer moving through it, or a microstructure, such as a micro pillar or a micro post, or some electrophoretic force configured to slow down the biopolymer movement, or a combination thereof.

11. The system of claim 10, wherein
the enzyme is a DNA or RNA polymerase or a helicase.

12. The system of claim 1, wherein
the said molecular wire comprises one of the following or a combination of them:
a) a molecule whose conductivity changes with conformation;
b) a natural nucleic acid that has a double helix structure mostly comprising G-C base pairs;
c) a natural nucleic acid that has a double helix structure, comprising modified base(s), modified nucleoside(s), or modified nucleotide(s);
d) a DNA analogue that forms a double helix structure, containing natural nucleobases;
e) a DNA analogue that forms a double helix structure, containing unnatural or synthetic nucleobases;
f) a DNA analogue that is composed of unnatural or synthetic bases and forms a double helix structure;
g) a DNA analogue that comprises a non-phosphate backbone;
h) a peptide that comprises an α helix or a β sheet structure, containing aromatic amino acids and charged amino acids;
i) a peptide that contains unnatural or synthetic aromatic amino acids; or
i) a peptide that comprises a non-amide backbone;
and the said receptor comprises one of the following or a combination of them:
a) a planar structure that can interact with the biopolymer through hydrogen bonding or aromatic stacking;
b) a moiety that is composed of two planar structures linked together by a spacing molecule, which can interact with a chemical entity through hydrogen bonding, aromatic stacking, or both hydrogen bonding and aromatic stacking;
c) a structure that interacts with DNA or RNA nucleobases through hydrogen bonding or base stacking;
d) a molecular cleft that traps DNA or RNA nucleobases in its cavity;
e) a molecular tweezer or clip that captures DNA or RNA nucleobases through hydrogen bonding and base stacking; or
f) any molecule that can distinguish among nucleobases by forming different noncovalent complexes that have different bonding energies.

13. The system of claim 1, wherein
the said anchoring molecules comprise the following or a combination of them:
a) a molecule that contains an amino group or groups;
b) a molecule that contains a thiol group or groups;
c) a molecule that contains a disulfide group or groups; or
d) a molecule that contains a diol group or groups.

14. The system of claim 1, wherein
the anchoring molecules that comprise three prongs or legs that forms a steady and firm attachment of the molecular wire to the electrodes.

15. The system of claim 1, wherein
the two electrodes have the same material or different materials, comprising the following or a combination of them:
a) a metal electrode that can directly react with the anchoring molecules;
b) a metal electrode that can be functionalized on their surfaces by self-assembling monolayers that can react with anchoring molecules to form covalent bonds;
c) a metal oxide electrode that can be functionalized with silanes that can react with anchoring molecules to form covalent bonds; or
d) a carbon electrode that can be functionalized with organic reagents that can react with anchoring molecules to form covalent bonds.

16. The system of claim 15, wherein
the said monolayers are formed by one of the following or a combination of them:
a) an organic molecule that contains a thiol group with a length of about 0.2 to about 3 nm;
b) an organic molecule that contains multiple thiol groups with a length of about 0.2 to about 3 nm;
c) an organic molecule that contains a functional group that can react with metal-specific anchoring molecules;
d) a thiol tripod that forms monolayers on a surface of the metal electrode and reacts with metal-specific anchoring molecules; or
e) a mixture of the said organic molecules or a mixture of the said organic molecules and the thiol tripod.

17. The system of claim 1, further comprising
additional one or more pairs of electrodes embedded in the nanopore for multiple measurements of the biopolymer when it passes through the nanopore or nanochannel.

18. The system of claim 1, wherein
the nanogap separating the two electrodes has the size of about 3 nm to about 1 um, and the molecular wire has length comparable to the nanogap, facilitating the formation of a bridge between the pair of electrodes.

* * * * *